(12) United States Patent
Needham et al.

(10) Patent No.: US 6,533,786 B1
(45) Date of Patent: Mar. 18, 2003

(54) ANTERIOR CERVICAL PLATING SYSTEM

(75) Inventors: Dusty Anna Needham, Lakeland, TN (US); Jeffrey Wade Poyner, Atoka, TN (US); Harry N. Herkowitz, West Bloomfield, MI (US); Thomas A. Zdeblick, Middleton, WI (US)

(73) Assignee: SDGI Holdings, Inc., Wilmington, DE (US)

( * ) Notice: Subject to any disclaimer, the term of this patent is extended or adjusted under 35 U.S.C. 154(b) by 0 days.

(21) Appl. No.: 09/417,402

(22) Filed: Oct. 13, 1999

(51) Int. Cl.⁷ .............................................. A61B 17/70
(52) U.S. Cl. ........................................................ 606/61
(58) Field of Search .............................. 606/61, 60, 69, 606/70

(56) References Cited

U.S. PATENT DOCUMENTS

| | | | |
|---|---|---|---|
| 3,386,437 A | | 6/1968 | Treace |
| 3,659,595 A | * | 5/1972 | Haboush |
| 3,741,205 A | | 6/1973 | Markolf et al. |
| 3,779,240 A | | 12/1973 | Kondo |
| RE28,841 E | | 6/1976 | Allgower et al. |
| 4,102,339 A | | 7/1978 | Weber et al. |
| 4,119,092 A | | 10/1978 | Gil |
| 4,408,601 A | | 10/1983 | Wenk |

(List continued on next page.)

FOREIGN PATENT DOCUMENTS

| | | |
|---|---|---|
| CH | 373 516 | 1/1964 |
| CH | 462 375 | 10/1968 |
| CH | 468 824 | 4/1969 |
| CH | 566 767 | 9/1975 |
| CH | 600 862 | 6/1978 |
| CH | 611 147 | 5/1979 |
| CH | 613 616 | 10/1979 |
| CH | 613 858 | 10/1979 |
| DE | 44 09 833 A1 | 10/1995 |
| EP | 0 016 338 | 10/1980 |
| EP | 0 382 256 | 8/1990 |
| EP | 0 705 572 A2 | 4/1996 |
| FR | 1505513 | 11/1966 |
| FR | 1 505 513 | 11/1967 |
| FR | 2 233 973 | 1/1975 |
| FR | 2 480 106 | 4/1981 |
| FR | 2 778 088 | 11/1999 |
| GB | 1 153 090 | 5/1969 |
| GB | 23 40 880 | 8/1973 |
| GB | 1 601 383 | 10/1981 |
| WO | WO 98/34553 | 8/1998 |
| WO | WO 98/34556 | 8/1998 |
| WO | WO 99/04718 | 2/1999 |

OTHER PUBLICATIONS

U.S. patent application Ser. No. 09/692,894, Assaker et al., filed Oct. 20, 2000.
Lowery, L. Gary, "Orion Anterior Cervical Plate System," pp. 1–25, 1995.

(List continued on next page.)

*Primary Examiner*—Jeffrey A. Smith
(74) *Attorney, Agent, or Firm*—Sterne, Kessler, Goldstein & Fox P.L.L.C.

(57) ABSTRACT

The present invention is directed to a system for anterior fixation of the spine that utilizes an elongated fixation plate. The plating system stabilizes the spine and promotes fusion and incorporation of a graft or implant in a portion of the spinal column. In one aspect of the invention, the fixation plate has a first end with a pair of holes. Bone screws extend through the holes to rigidly secure the plate to a first vertebra. The second end of the plate is provided with a pair of slots through which bone screws extend for engagement with a second vertebra. The screws extending through the slots are translatable in the slot to maintain compression of the spinal column portion. The plating system includes a retainer assembly that prevents screw back out. Methods and instruments relating to the plating system are also described.

92 Claims, 22 Drawing Sheets

U.S. PATENT DOCUMENTS

| | | |
|---|---|---|
| 4,484,570 A | 11/1984 | Sutter et al. |
| 4,488,543 A | 12/1984 | Tornier |
| 4,493,317 A | 1/1985 | Klaue |
| 4,503,848 A | 3/1985 | Caspar et al. |
| 4,513,744 A | 4/1985 | Klaue |
| 4,957,497 A * | 9/1990 | Hoogland et al. ............ 606/71 |
| 4,959,065 A | 9/1990 | Arnett et al. |
| 5,041,113 A | 8/1991 | Biedermann et al. |
| 5,041,116 A | 8/1991 | Wilson |
| 5,057,111 A | 10/1991 | Park |
| 5,108,395 A | 4/1992 | Laurain |
| 5,127,912 A | 7/1992 | Ray et al. |
| 5,127,914 A | 7/1992 | Calderale et al. |
| 5,147,361 A | 9/1992 | Ojima et al. |
| 5,180,381 A | 1/1993 | Aust et al. |
| 5,261,910 A | 11/1993 | Warden et al. |
| 5,300,073 A | 4/1994 | Ray et al. |
| 5,324,290 A | 6/1994 | Zdeblick et al. |
| 5,364,399 A | 11/1994 | Lowery et al. |
| 5,380,328 A | 1/1995 | Morgan |
| 5,423,826 A | 6/1995 | Coates et al. |
| 5,492,442 A | 2/1996 | Lasner |
| 5,545,166 A | 8/1996 | Howland |
| 5,549,612 A | 8/1996 | Yapp et al. |
| 5,558,674 A | 9/1996 | Heggeness et al. |
| 5,578,034 A | 11/1996 | Estes |
| 5,601,553 A | 2/1997 | Trebing et al. |
| 5,607,426 A | 3/1997 | Ralph et al. |
| 5,616,144 A | 4/1997 | Yapp et al. |
| 5,620,443 A | 4/1997 | Gertzbein et al. |
| 5,676,666 A | 10/1997 | Oxland et al. |
| 5,681,311 A * | 10/1997 | Foley et al. ................... 606/61 |
| 5,800,433 A | 9/1998 | Benzel et al. |
| 5,904,683 A | 5/1999 | Pohndorf et al. |
| 5,951,558 A | 9/1999 | Fiz |
| 6,017,345 A | 1/2000 | Richelsoph |
| 6,129,730 A | 10/2000 | Bono et al. |
| 6,139,550 A | 10/2000 | Michelson |
| 6,193,721 B1 | 2/2001 | Michelson |
| 6,224,602 B1 | 5/2001 | Hayes |
| 6,235,034 B1 * | 5/2001 | Bray ............................ 606/71 |

OTHER PUBLICATIONS

"Casper Anterior Cervical Fusion Instrumentation and Trapezial Osteosynthetic Plates," by Dr. Wolfhard Caspar, Date Unknown.

"Codman Codman Anterior Cervical Plate System", Date Unknown.

"Cervi–Lok Cervical Fixation System Surgical Technique Manual," Spine–Tech, Date Unknown.

"Bone–implant interface structures after nontapping and tapping insertion of screw–type titanium alloy endosseous implants," Satomi, Keiichi, DDS et al., *The Journal of Prosthetic Dentistry*, Mar. 1988, V59, No. 3, p. 339–342.

"Comparison of Compression and Torque Measurements of Self–Tapping and Pretapped Screws," Phillips, John H., et al., *Plastic and Reconstructive Surgery*, Mar. 1989, V83, No. 3 p. 447–456.

"Spinal Instrumentation," An, Howard S., et al., Williams & Wilkins, 1992, p. 1–11, 49–60, 167–196, 257–280, 379–411.

"Cervical Plate–Cage Systems," Scient'x, Date unknown.

"Cervical Spine Locking Plate," Synthes, 1995.

"The Aline Anterior Cervical Plate," Smith & Nephew Orthopaedics, Date Unknown.

"AcroPlate Anterior Cervical System," AcroMed, 1994.

"Dynamic Compression Plate," pp. 70–79, Author Unknown, Date Unknown.

"An Impacting Bone Plate," Bagby, George W., et al., from Staff Meetings of the Mayo Clinic, vol. 32, No. 3; pp. 55–57, Feb. 6, 1957.

"The Effect of Compression on the Rate of Fracture Healing using a Special Plate," Bagby, George W. et al.; *American Journal of Surgery*; vol. 95, pp. 761–771, May 1958.

"The Use of my Compression Plate for Osteosyntheses of the Various Types of Femoral Intertrochanteric Osteotomies;" Bertolin, Translation from Italian of a paper presented at the Congress of the Society of Orthopaedics and Traumatology of the Medical Union of the Latin Mediterranean; Jun. 6–7, 1965.

* cited by examiner

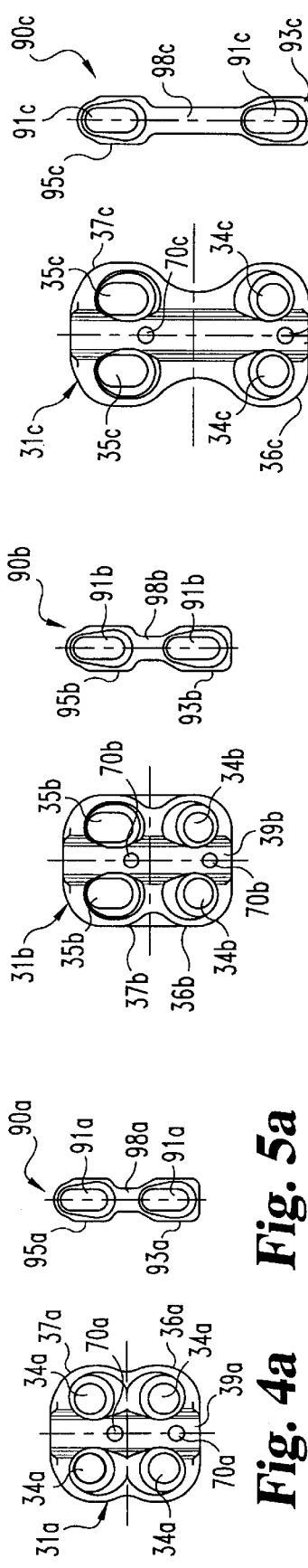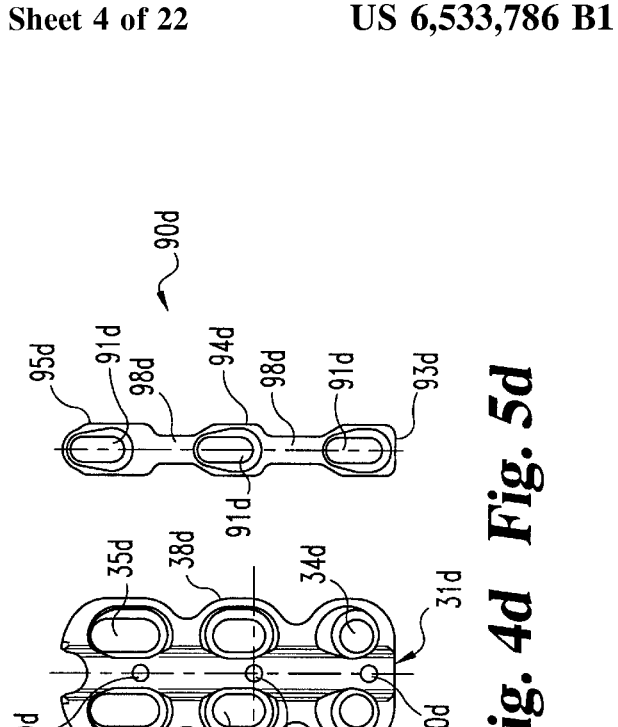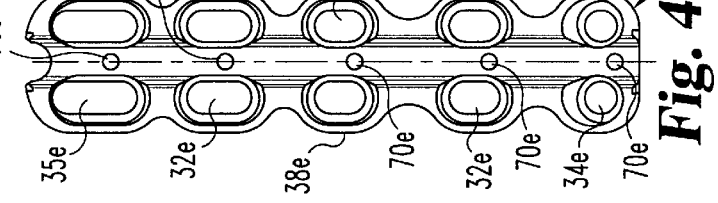

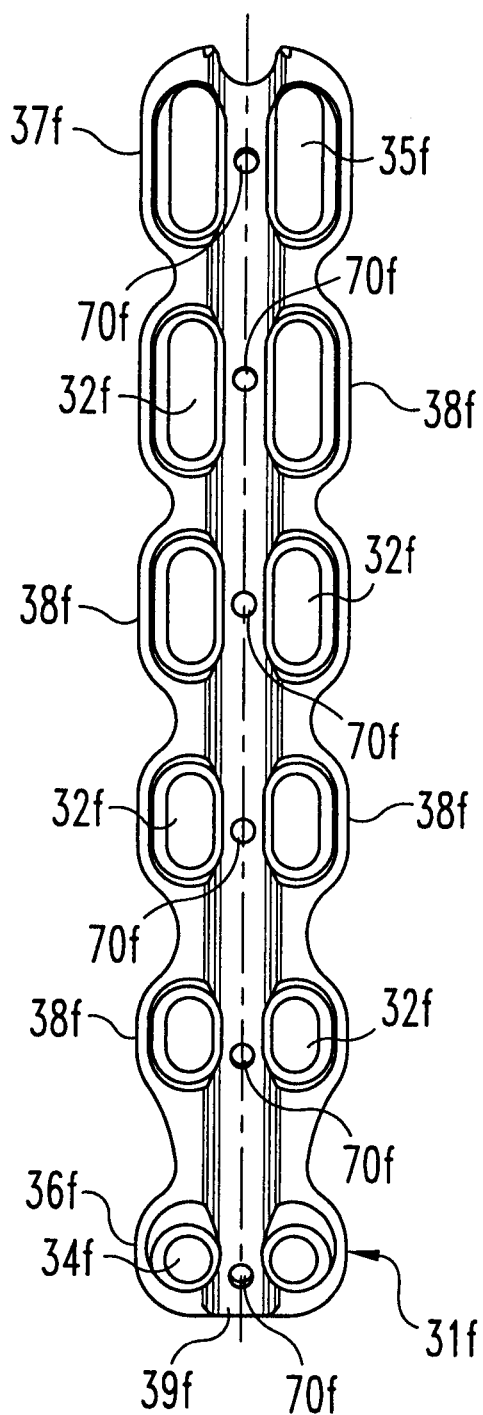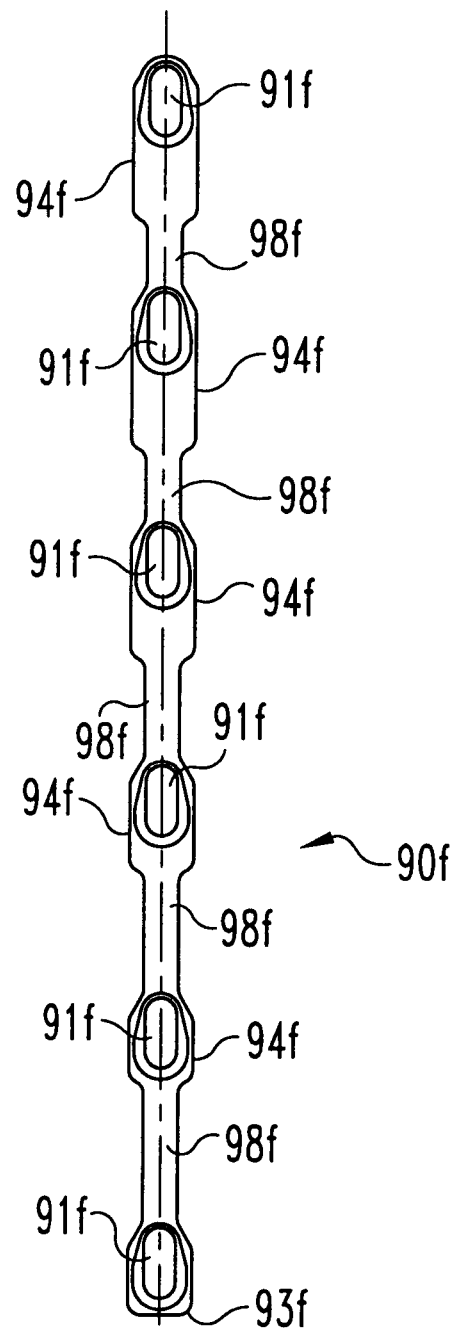
*Fig. 4f*  *Fig. 5f*

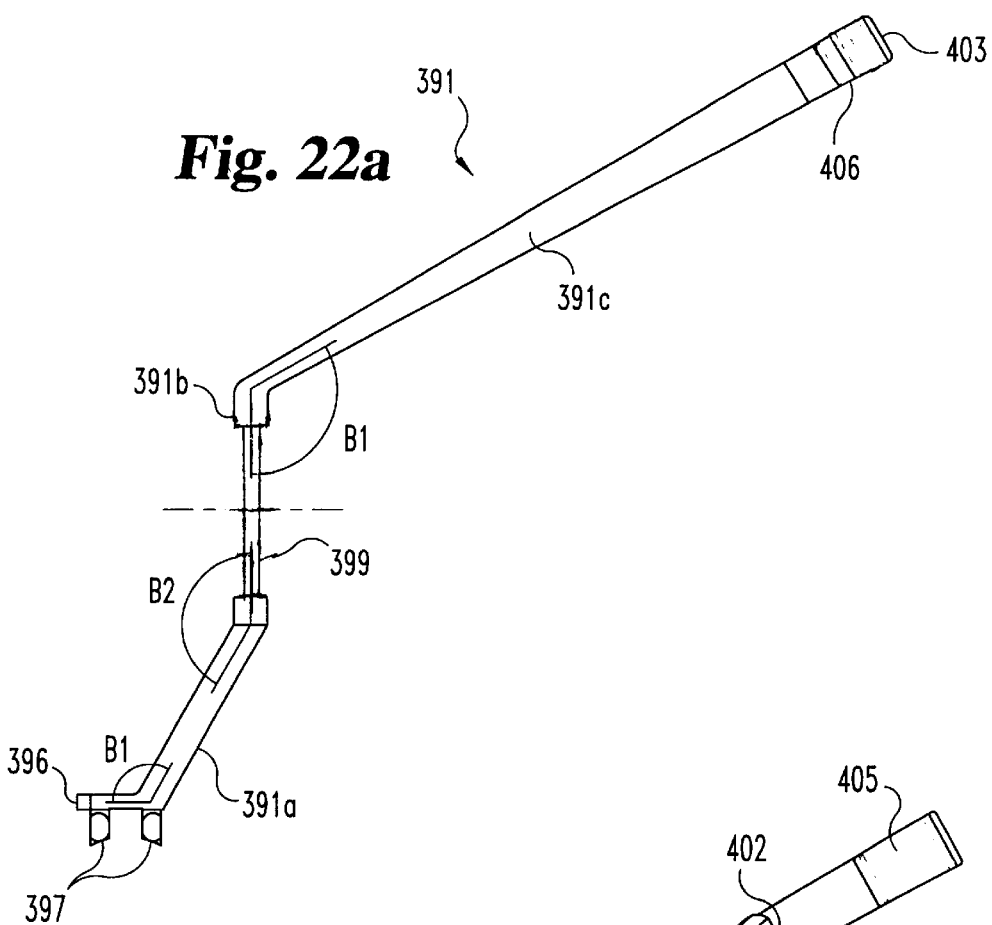
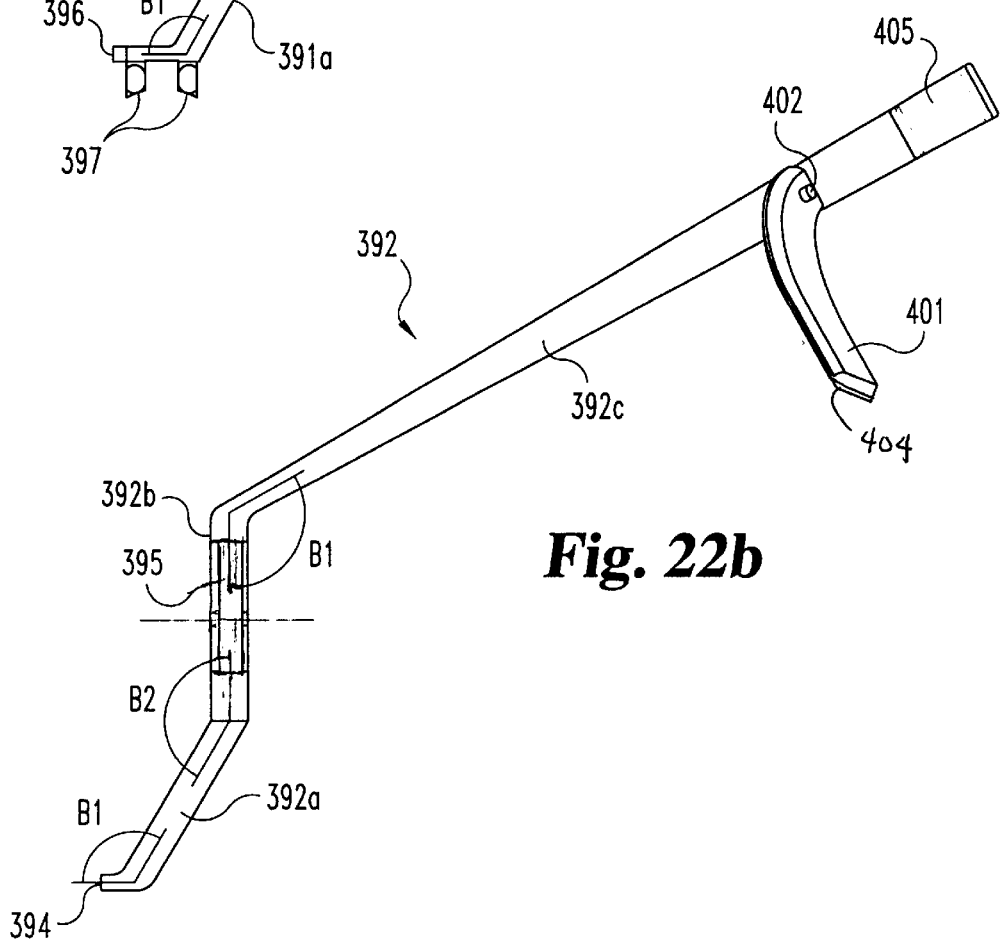

ANTERIOR CERVICAL PLATING SYSTEM

BACKGROUND OF THE INVENTION

The present invention relates generally to the field of instrumentation and systems for the spine, and more particularly to instrumentation and systems for use in treatment of various pathologies of the cervical spine.

As with any bony structure, the spine is subject to various pathologies that compromise its load bearing and support capabilities. Such pathologies of the spine include, for example, degenerative diseases, the effects of tumors and, of course, fractures and dislocations attributable to physical trauma. Spinal surgeons have addressed these problems using a wide variety of instrumentation in a broad range of surgical techniques. The use of elongated rigid plates has been helpful in the stabilization and fixation of the lower spine, most particularly in the thoracic and lumbar spine. These same plating techniques have found some level of acceptance by surgeons specializing in the treatment of the cervical spine.

The cervical spine can be approached either anteriorly or posteriorly, depending upon the spinal disorder or pathology to be treated. Many well-known surgical exposure and fusion techniques of the cervical spine are described in the publication entitled *Spinal Instrumentation*, edited by Drs. Howard An and Jerome Cotler. This text also describes instrumentation that has been developed in recent years for the cervical spine. Plating systems have become predominant for providing internal instrumentation in techniques that achieve fusion of the cervical spinal from an anterior approach.

During the development of cervical plating systems, particularly for the anterior approach, various needs have been recognized. For example, the system should provide strong mechanical fixation that can control movement of each vertebral segment. The system should be able to withstand axial loading and continuity with each of the three columns of the spine. The system should also be able to maintain stress levels below the endurance limits of the plate material, while at the same time exceeding the strength of the anatomic structures or vertebrae to which the plating system is engaged. The thickness of the system should be small to lower its prominence, particularly at the smaller spaces of the cervical spine. Also, the screws used to connect the plate to the vertebrae must not loosen over time or back out from the plate.

While the plating system should satisfy certain mechanical requirements, the system should also satisfy certain anatomic and surgical considerations. For example, the cervical plating system should minimize the intrusion into the patient and reduce the trauma to the surrounding soft tissue. This is particularly important in such procedures that relate to the cervical spine because the complications can be very devastating, such as injury to the brain stem, spinal cord, or vertebral arteries. It has also been found that the optimum plating system permits placement of more than one screw in each of the instrumented vertebrae. Also, the system should be designed to contact the vertebrae for greater stability.

Many spinal plating systems have been developed in the last couple of decades to address some of the needs and requirements for cervical fixation systems. However, even with the more refined plating system designs, there still remains a need for a system that effectively addresses the requirements for such a system.

There is also a need for a plating system that addresses procedures designed to achieve fusion of the cervical spine. In cases where a graft or implant is implanted to maintain a disc space and/or replace one or more diseased vertebral bodies, it is desirable to increase the rate of fusion and incorporation of the graft or implant into the spine. A plating system that allows pre-loading of the graft or implant and/or provides continual loading thereafter is preferred.

While the prior art plating systems relating to cervical plating systems are steps in the right direction, there remains a need for additional improvements. The present invention is directed to satisfying these needs, among others.

SUMMARY OF THE INVENTION

The present invention contemplates a system for anterior fixation of the spine that utilizes an elongated fixation plate. In one aspect of the invention, the plating system promotes fusion and incorporation of a graft or implant in a spinal column portion. The plating system provides continual loading of the graft or interbody implant. In another aspect, the plating system allows a compressive load to be applied to the spinal column portion. This pre-loading and continual loading avoids stress-shielding and promotes fusion and incorporation of the graft or implant into the spinal column portion.

In one aspect of the invention, the fixation plate has a first end with a pair of holes. Bone engaging fasteners extend through the holes to rigidly secure the plate to a first vertebra. A second end of the plate is provided with a pair of slots through which bone engaging fasteners extend for engagement with a second vertebra. The bone engaging fasteners extending through the slots are translatable in the slots to allow settlement and compression of the second vertebra with respect to the first vertebra. In a preferred embodiment, the plating system includes a retainer assembly that prevents fastener back out.

According to another aspect of the invention, a bone fixation system for a spinal column segment is provided. The bone fixation system includes a plate with a central axis, a length between a first end and a second end, and top and bottom surfaces. The plate defines a plurality of first openings and a plurality of second openings between the top and bottom surfaces. At least one of the plurality of first openings is positioned adjacent the first end of the plate and defines a circular hole though the plate. At least one of the plurality of second openings is positioned adjacent the second end of the plate and defines a slotted hole having a first width and a first length adjacent the bottom surface. A number of bone engaging fasteners extend through the first and second openings. Each bone engaging fastener has a threaded shank and an enlarged head. The fastener has a substantially cylindrical portion with a third diameter that interfaces with the plate in the first opening such that the fastener inserted in the first opening assumes a fixed orientation with the plate. The head of said bone engaging fastener inserted into the second opening is translatable along the length of the second opening to maintain compression of the spinal column portion.

In another aspect of the invention, a bone fixation system for a spinal column portion is provided. The bone fixation system includes a plate with a length along a central axis that extends between a first end and a second end. The plate has a top surface and a bottom surface and defines a plurality of first and second openings between the surfaces. At least a pair of the first openings is positioned adjacent the first end, and the first openings define a circular opening having a first diameter. At least a pair of the second openings is positioned adjacent the second end, and the second openings define a slot having a first width and a first length. A number of bone engaging fasteners with an elongated threaded shank and an enlarged head are provided. The bone engaging fasteners extend through the first and second holes from the top surface. A retainer assembly retains the bone engaging fasteners in the first and second openings. In one form, the retainer assembly includes a washer having a length that substantially corresponds to the length of the plate.

In yet another aspect of the invention, a bone fixation system for a spinal column segment is provided. The system includes four bone engaging fasteners that have an enlarged head and a threaded shank. An elongated plate has a length extending between a first end and a second end sized to span between at least two vertebrae. The plate defines one pair of holes adjacent the first end and one pair of slots adjacent the second end. Each of the holes and the slots are configured to receive the threaded shank of a corresponding one of the bone engaging fasteners therethrough to engage the plate to the vertebrae. The bone engaging fasteners extend through the pair of holes to fix the plate to the first vertebra. Bone engaging fasteners extend through the pair of slots to secure the plate to the second vertebra. The bone engaging fasteners axially translate in the slots to maintain compression on the spinal column portion.

In a further aspect of the invention, a bone fixation system for a spinal column portion is provided. The system includes six bone engaging fasteners that each have an enlarged head and a threaded shank. An elongated plate extending between a first end and a second end has a length sized to span between at least three vertebrae. The plate defines one pair of holes over a first vertebra, one pair of slots over a second vertebra, and one pair of intermediate slots over a third vertebra intermediate the first and second vertebrae. The holes and the slots are configured to receive the threaded shank of the bone engaging fasteners therethrough. The bone engaging fasteners extend through the pair of holes to fix the plate to the first vertebra. The bone engaging fasteners extend through the slots to secure the plate to the second vertebra. The bone engaging fasteners axially translate in the slots to maintain compression on the spinal column portion. The surgeon can optionally place bone engaging fasteners in the intermediate slots to engage the plate to the third vertebra.

In another aspect of the invention, there is provided a retainer assembly for an elongated plate that extends between at least two vertebrae. The retainer assembly includes a washer having at least one tapered aperture. The washer is translatable between a locked position and an unlocked position by threading a locking fastener into the tapered aperture.

In another aspect of the invention, there is provided a retainer assembly for an elongated plate that extends between at least two vertebrae. The plate defines a number of openings for insertion of bone engaging fasteners to attach the plate to the at least two vertebrae. The plate further includes a first fastener bore in the plate adjacent at least one of the openings positioned over the first vertebra and a second fastener bore in the plate adjacent at least one of the openings positioned the second vertebra. The retainer assembly includes a washer that defines at least a first aperture adjacent the at least one opening positioned over the first vertebra and a second aperture adjacent the at least one opening positioned over the second vertebra. A locking fastener for each of the apertures in the washer has an elongated shank extending through the aperture configured to engage the fastener bore of the plate. The washer is movable between a first position where the bone engaging fasteners are insertable into each of the at least one openings and a second position where the washer has a surface configured to contact the head of a bone engaging fastener extending through the at least one opening positioned over the first vertebra and overlap the head of a bone engaging fastener extending through the at least one opening positioned over the second vertebra.

In another aspect of the invention, a retainer assembly for an elongated plate is provided. The plate extends between at least two vertebrae and defines a number of openings for insertion of bone engaging fasteners to secure the plate to the at least two vertebrae. The plate includes at least one first fastener bore. The retainer assembly includes a washer that defines at least a first aperture positioned in communication with the at least one fastener bore. A locking fastener extends through the first aperture and has an elongated shank to engage the fastener bore of the plate. The washer is movable along its central axis between a first position where the at least two bone engaging fasteners are inserted through the openings to engage the first and second vertebrae and a second position where a surface of the washer contacts at least the head of the bone engaging fasteners engaged to the first vertebra.

In another aspect of the present invention, a method for applying a compressive load to a number of vertebrae including at least a first vertebra and a second vertebra is provided. The method includes: (a) providing a template having a guide surface and a notch; (b) positioning the template on the second vertebra with the guide surface on an endplate of the second vertebra to locate the template notch on the body of the second vertebra; (c) inserting a pin through the notch of the template into the body of the second vertebra; (d) removing the template; (e) placing a sleeve over the pin; (f) providing a plate having a length extending between a first end and a second end, the plate including a notch on the second end and a number of openings therethrough; (g) placing the plate on the vertebral segment with the sleeve nested in the notch of the plate; (h) fixing the first end of the plate to the first vertebra with bone engaging fasteners extending through the openings positioned over the first vertebra; (i) removing the sleeve from the pin to form a gap between the pin and the notch in the plate; (j) connecting a compression tool to the pin and the plate; and (k) applying a compression load to the vertebral segment with the compression tool until the pin contacts the notch. In one embodiment, the plate includes holes positioned over the first vertebra and slots positioned over the second vertebra. In another embodiment, the method further includes the step of retaining the bone engaging fasteners in the plate with a retainer assembly.

In another aspect of the present invention, there is provided a method for maintaining compression of a spinal column portion. The method includes: (a) providing a plate having a length between a first end and a second end sized to span at least two vertebra, the plate having a pair of holes at the first end positioned over the first vertebra and a pair of slots at the second end positioned over the second vertebra; (b) fixing the first end of the plate to the first vertebra with bone engaging fasteners extending through the pair of holes; (c) securing the second end of the plate to the second plate with bone engaging fasteners extending through the pair of slots; and (d) translating the bone engaging fasteners in the slots to allow settling of the spinal column segment. In one embodiment, the method further includes retaining the bone engaging fasteners in the plate with a retainer assembly.

BRIEF DESCRIPTION OF THE DRAWINGS

FIGS. 4(a)–(f) are top plan views of fixation plates of the present invention provided in different sizes and configurations.

FIGS. 5(a)–(5f) are top plan views of washers of the present invention provided in sizes and configurations corresponding to the plates in FIGS. 5(a)–5(f).

FIGS. 22(a)–22(b) are side elevational views of the arms of an alternate embodiment compression tool.

DESCRIPTION OF THE PREFERRED EMBODIMENTS

Figure 1:
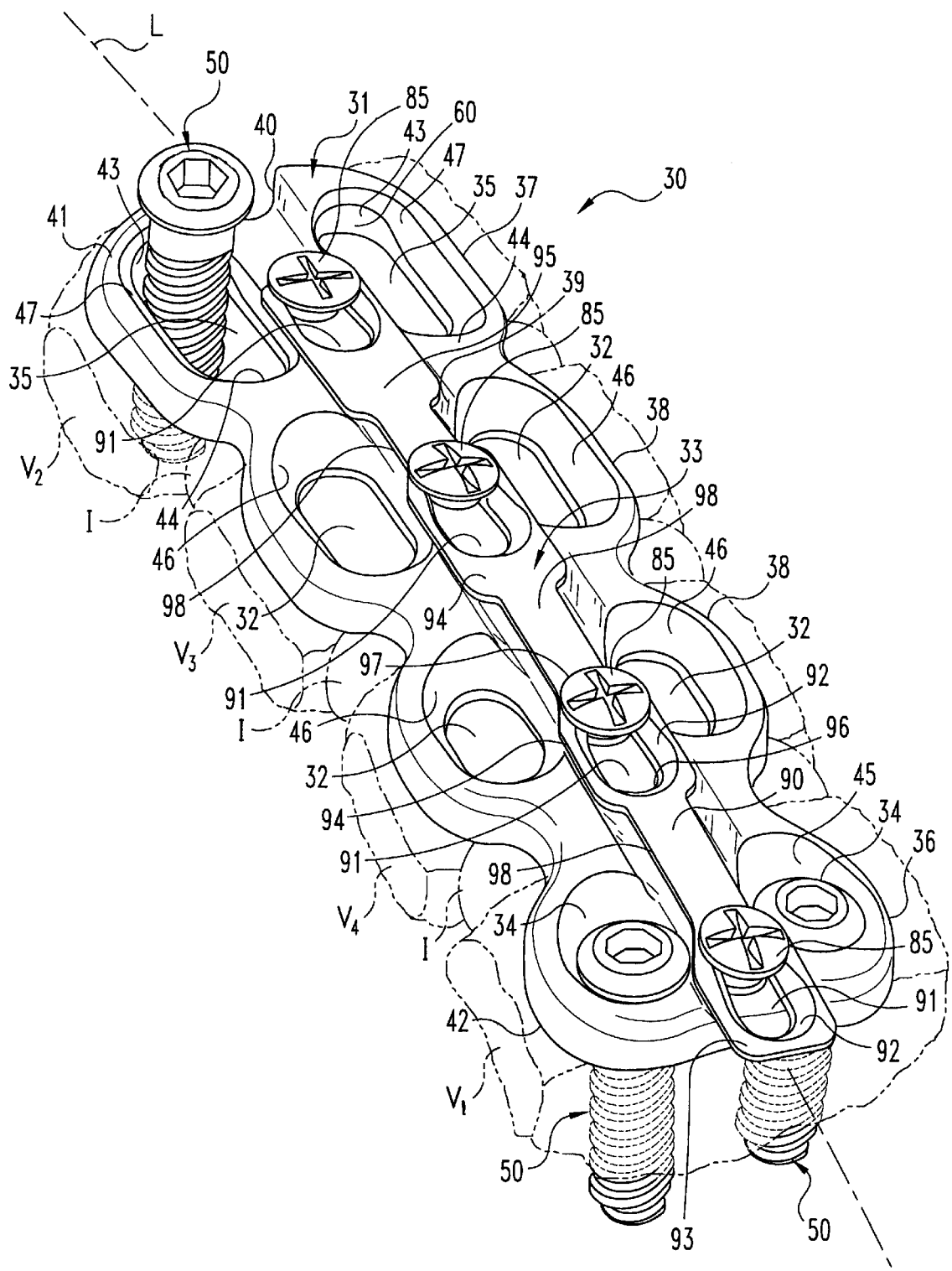
FIG. 1 is a top perspective view of an anterior plating system according to the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the illustrated devices, and any further applications of the principles of the invention as illustrated herein, are contemplated as would normally occur to one skilled in the art to which the invention relates.

Figure 2:
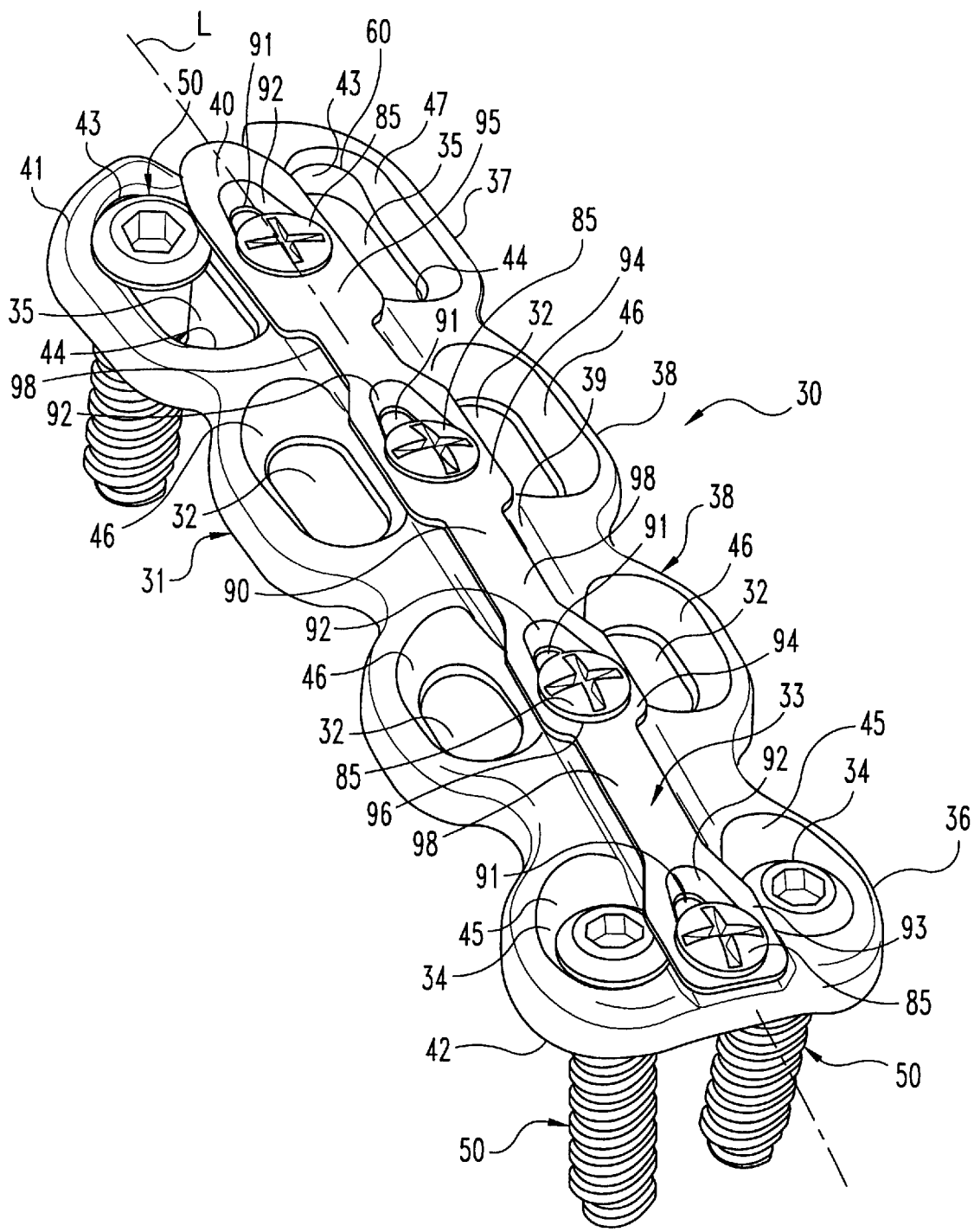
FIG. 2 is a top perspective view of the anterior plating system of FIG. 1 with the bone screws locked in place.
Figure 3:
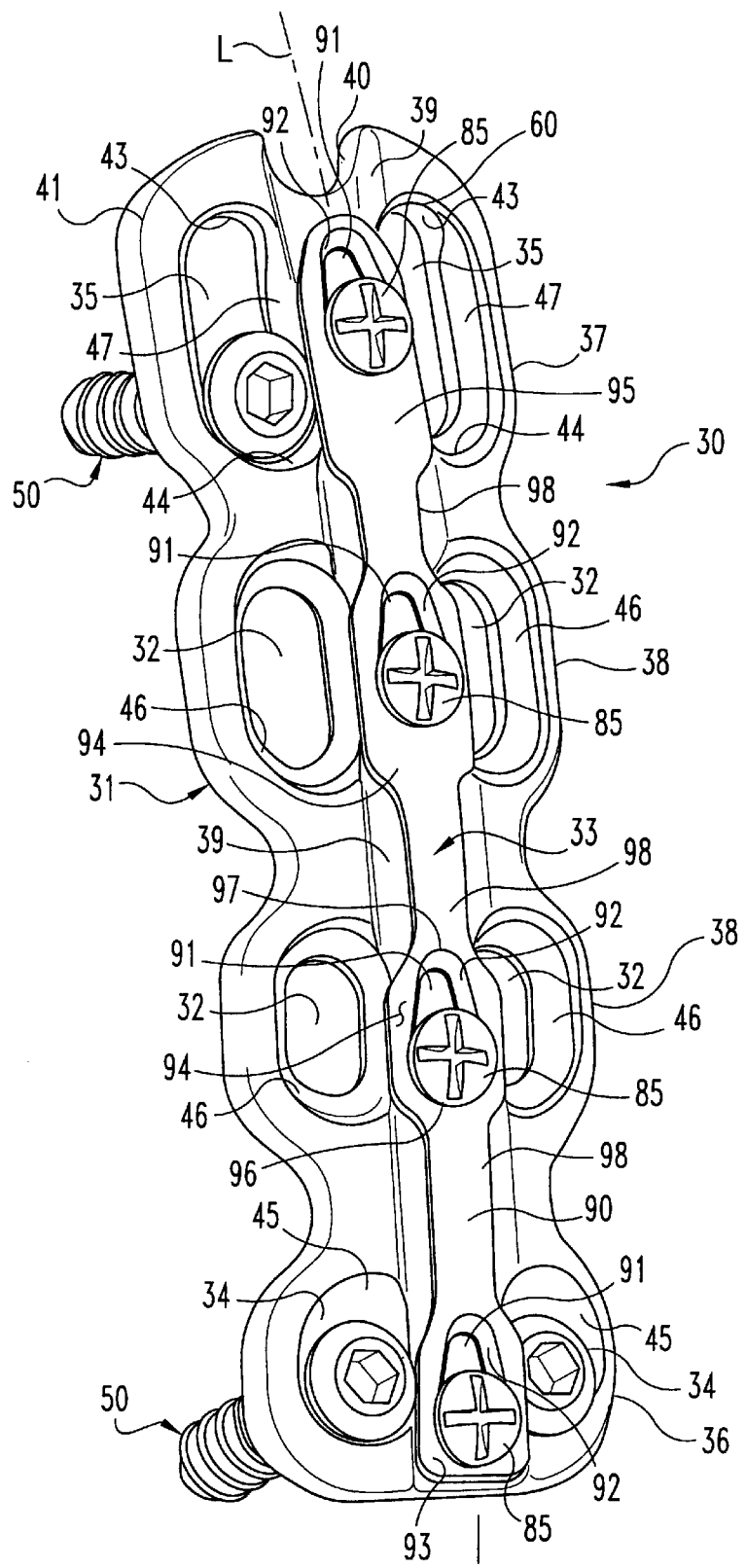
FIG. 3 is a top perspective view of the anterior plating system of FIG. 1 with bone screws translated in a slot of the plate.

A plating system 30 having application in an anterior approach to the cervical spine is depicted in FIGS. 1–3. The portion of the spine is shown schematically in FIG. 1 to include a first vertebra V1, a second vertebra V2, and intermediate vertebrae V3 and V4. Preferably, first vertebra V1 is the inferior or bottom vertebra in the portion of the spinal column and the second vertebra V2 is the superior or top vertebra of the portion of the spinal column. However, it is also contemplated herein that first vertebra V1 is the superior vertebra and that second vertebrae V2 is the inferior vertebra. It should also be understood that, as described below, the present invention has application with spinal column portions that include vertebrae ranging in number from two to six vertebrae. One or more implants I may be placed into one or more of the disc spaces between adjacent vertebrae as needed. Implant I may be a bone graft, fusion device, or any other type of interbody device that is insertable into a disc space and promotes fusion between adjacent vertebrae.

In accordance with the present invention, the plating system 30 includes an elongated plate 31 having a number of openings therethrough and a number of bone engaging fasteners, shown in the form of bone screws 50, that are insertable through the openings. In a preferred form, each bone engaging fastener is in the form of a bone screw. Plate 31 has a longitudinal axis L extending along the length of the plate at its centerline. Bone engaging fasteners or bone screws 50 are held in plate 31 by way of a retainer assembly 33 positioned along axis L. The openings of elongated plate 31 include a pair of holes 34 at first node 36 adjacent a first end of plate 31. First node 36 is positioned over first vertebra V1. Plate 31 also includes a pair of slots 35 at a second node 37 adjacent a second end of plate 31. Second node 37 is positioned over second vertebra V2. In some forms of plate 31, several intermediate nodes 38 are provided along the length of the plate 31 between first node 36 and second node 37. Each intermediate node 38 includes a pair of intermediate slots 32 positioned over a corresponding one of the intermediate vertebrae V3 and V4. Plating system 30 can be fabricated from any type of biocompatible material.

It is preferred that holes 34 are paired with one of the holes of the pair on one side of the longitudinal axis L and the other hole of the pair on the opposite side of axis L. Slots 32 and 35 are similarly arranged in pairs. It is also preferred that paired holes 34 are identical in shape and size, and are located symmetrically about the axis L. Paired slots 35 are also identical in shape and size, and are located symmetrically about the axis L. The paired slots 32 at intermediate nodes 38 are also identical in shape and size, and are located symmetrically about the axis L. Plate 31 includes recesses between each of nodes 36, 37, 38 to reduce the outer contouring size of the plate. In addition, the recesses between each of the nodes provides an area of reduced material, allowing additional bending of the plate by the surgeon as may be required by the spinal anatomy. Plate 31 has a length selected by the surgeon with nodes 36, 37, and, if needed, nodes 38 to register with the patient vertebrae.

Plate 31 preferably includes a rounded upper surface 41 that is in contact with the soft tissue surrounding the spine when the plate is engaged to the spine. Rounded surface 41 reduces the amount of trauma that would be experienced by the surrounding soft tissue. The bottom surface 42 of plate 31 is preferably configured to contact the vertebral bodies of the spine at each of the instrumented levels. In one embodiment, at least a portion of bottom surface 42 can be textured along the length of the plate to enhance its grip on a vertebral body.

Holes 34 include a recess 45 adjacent the top surface of plate 31 that allow the head of the bone engaging fastener, such as bone screw 50, to be countersunk in plate 31. Similarly, intermediate slots 32 include a recess 46 around each slot 32 adjacent top surface of the plate, and slots 35 include a recess 47 around each slot 35 adjacent the top surface of the plate. Preferably, slots 35 include a ramp 60 that, as described further below, allows a dynamic compression load to be applied to the spinal column portion upon insertion of screw 50 at second end 43 of slot 35. Recesses 46, 47 also allow the head of screw 50 to be countersunk in plate 31 when inserted through a corresponding one of the slots 32, 35. A groove 39 extends along axis L of plate 31 and intersects with each of recesses 45, 46, 47 along the length of groove 39. The end of plate 31 at second node 37 includes a notch 40, which is preferably rounded with a radius R4 centered on axis L (Fig, 12.)

Retainer assembly 33 includes a washer 90 having a length that substantially corresponds to the length of plate 31. Washer 90 defines a plurality of apertures 91. Each aperture 91 is provided at a body portion 93, 94, 95 that corresponds to vertebral nodes 36, 37, 38, respectively. A connecting portion 98 extends between and connects body portions 93, 94, 95. Each of the apertures 91 has a countersink 92 extending therearound adjacent to the top surface of washer 90. As described more fully below, countersink 92 is tapered from a first width at the first end of aperture 91 to a second width at the second end of aperture 91, the first width being greater than the second width. Locking fasteners, shown in the form of screws 85, are positionable, each through a corresponding one of the apertures 91, to engage a fastener bore 70 (see FIGS. 4(a)–4(f)) in plate 31 and couple washer 90 to plate 31.

Consequently, retainer assembly 33 retains screws 50 placed into the vertebral bodies at each of the instrumented levels. Washer 90 is translatable from an unlocked position (FIG. 1) for bone screw insertion to a locked position (FIG. 2) after screw insertion to contact the head of the bone screws in holes 34 and overlap the heads of bone screws in slots 32, 35. Preferably, washer 90 does not contact the heads of bone screws in slots 32, 35, thus allowing translation of the bone screws in the slots. Back-out of the bone screws in slots 32, 35 is prevented when the bone screw backs out from its seated position a sufficient amount to contact washer 90. Preferably, washer 90 resides almost entirely within groove 39 of plate 31 to minimize the overall height of the construct.

As shown in FIG. 1, retainer assembly 33 is in an unlocked condition with screws 85 at the second end of apertures 90. In the unlocked condition, body portions 93, 94, 95 of washer 90 do not overlap holes 34 and a portion of slots 32, 35, and enable insertion of the bone screws 50 therein. Narrowed portions 98 of washer 90 allow bone screws 50 to be placed through holes 34 and slots 35 to secure plate 31 to the vertebrae V1 and V2. If desired, the surgeon can also place bone screws 50 in intermediate slots 32 to secure plate 31 to vertebrae V3 and V4 as deemed necessary. Plate 31 and bone screws 50 preferably interface in holes 34 such that rigid fixation of plate 31 to the first vertebra V1 is achieved. Slots 35 are positioned over second vertebra V2, and include a second end 43 and a first end 44. As shown in FIG. 1, screw 50 is initially is inserted at second end 43 of slot 35, allowing subsequent translation of screw 50 in slot 35 from second end 43 to first end 44. For the purposes of clarity, only a single screw 50 is shown in slot 35; however, it is contemplated that bone screws are inserted in both slots 35. Bone screws 50 inserted in intermediate slots 32 also translate from the second end 48 to first end 49 (FIG. 15) of slot 32.

Once screws 50 are placed through holes 34 and in slots 32 and 35, washer 90 of retainer assembly 33 may be translated to its locked condition shown in FIG. 2. In the locked condition, body portions 93, 94, 95 of washer 90 retain the heads of the inserted screws 50 in holes 34 and slots 32, 35 and prevent the screws from backing out of plate 31. In order to translate the retainer assembly 33 to its locked condition, locking screw 85 is threaded into a corresponding fastener bore 70 in plate 31. This downward threading of locking screw 85 causes the tapered countersink 92 of washer 90 to ride along the head of locking screw 85 until locking screw 85 contacts the first end of aperture 91. This translates washer 90 along axis L to its locked condition, where the washer 90 retains bone screws 50 in plate 31.

Bone screws 50 are allowed to translate within slots 35 and intermediate slots 32 from the second end of the slots to the first end of the slots while retainer assembly 33 retains bone screws 50 in plate 31 and prevents screw backout. As shown in FIG. 3, the screw positioned in slot 35 has translated from second end 43 to first end 44. The translation of screw 50 is limited by contact of screw 50 with first end 44. The amount of translation may also be controlled by providing bone screws in intermediate slots 32. Thus, the amount of translation of the spinal column segment can be limited by the length of slots 32, 35.

Referring now to FIGS. 4(a)–4(f) and FIGS. 5(a)–5(f), several embodiments of elongated plate 31 and washer 90 are depicted. It is understood that the anterior plating system 30 according to the present invention can be readily adapted for fixation to several vertebrae by modifying the length of plate 31 and the number and arrangements of holes 34, second slots 35, and intermediate slots 32. Paired slots 32, 35 and paired holes 34 at each of the vertebrae provide, at a minimum, for at least two bone screws 50 to be engaged into each respective vertebrae. The placement of two or more screws in each vertebral body improves the stability of the construct. It is one object of the present invention not only to provide for multiple screw placements in each vertebral body, but also to provide means for retaining the bone screws in plate 31 to prevent back out or loosening of the screws. The present invention contemplates various specific embodiments for a plate 31 that is provided in lengths that range from 19 millimeters (hereinafter "mm") to 110 mm, and an overall width of about 17.8 mm. However, other dimensions for the length and width of plate 31 are also contemplated herein.

The plate 31 of FIGS. 1–3 is sized to span four vertebrae and includes a first node 36, a second node 37, and two intermediate nodes 38. In FIGS. 4(a) and 5(a), plate 31a and washer 90a are sized span two vertebrae. Plate 31a has holes 34a at first node 36a and holes 34a at second node 37a. Plate 31a is provided with washer 90a that resides in groove 39a and is translatable to retain bone screws in holes 34a. In this embodiment, plate 31a provides rigid fixation at each vertebra. A modification of plate 31 a is depicted FIGS. 4(b) and 5(b). The holes at the second vertebral node are replaced with slots 35b at second node 37b. A washer 90b resides in groove 39b and is translatable to retain bone screws in holes 34b and slots 35b.

Plate 31c and washer 90c of FIGS. 4(c) and 5(c) similarly provide for instrumentation at two vertebrae. Plate 30c has a recess portion between nodes 36c and 37c. Washer 90c resides in groove 39c and is translatable to retain lock screws in holes 34c and slots 35c. It should be noted that the plates of FIGS. 4(a)–4(c) span two vertebrae, and preferably do not include notch 40 on the second end of that plate as do the plates sized to span three or more vertebrae.

Plate 31d and washer 90d of FIGS. 4(d) and 5(d) are provided for instrumentation at three vertebrae. Plate 31d has first vertebral node 36d, second vertebral node 37d, and intermediate node 38d. Washer 90d resides in groove 39d and is translatable to retain bone screws in holes 34d and slots 32d, 35d. Plate 31e and washer 90e of FIGS. 4(e) and 5(e) are provided for instrumentation at five vertebrae. Plate 31e has first vertebral node 36e, second vertebral node 37e, and three intermediate nodes 38e. Washer 90e resides in groove 39e and is translatable to retain bone screws in holes 34e and slots 32e, 35e. Plate 31f and washer 90f of FIGS. 4(f) and 5(f) are provided for instrumentation at six vertebrae. Plate 31f has first vertebral node 36f, second vertebral node 37f, and four intermediate nodes 38f. Washer 90f resides in groove 39f and is translatable to retain bone screws in holes 34f and slots 32f, 35f.

Figure 6:
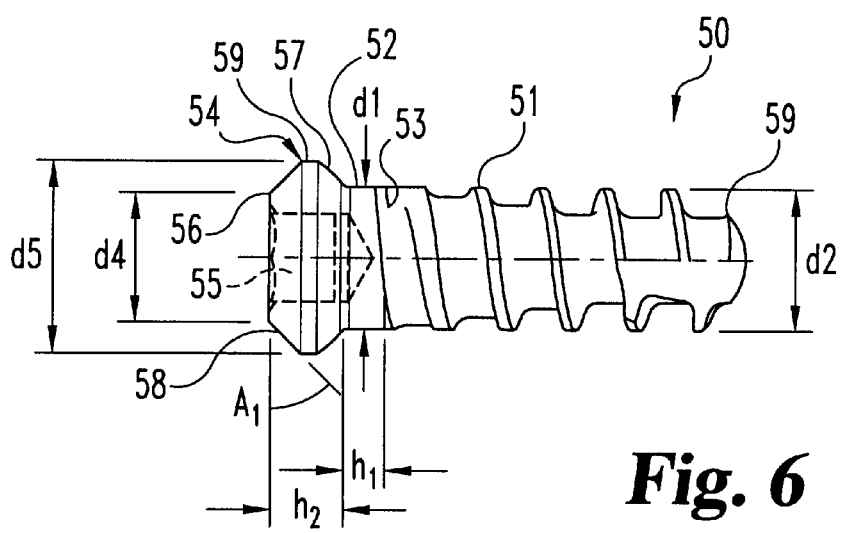
FIG. 6 is a side elevational view of a bone screw according to one aspect of the present invention.

Referring now to FIG. 6, the details of bone engaging fastener or screw 50 are shown. Bone screw 50 is preferably configured for engagement in the cervical spine, and includes threaded shank 51 that is configured to engage a cancellous bone of the vertebral body. The threaded shank may be provided with self-tapping threads, although it is also contemplated that the threads can require prior drilling and tapping of the vertebral body for insertion of screw 50. It is preferred that the threads on shank 51 define a constant outer diameter d2 along the length of the shank. It is also preferred that shank 51 has a root diameter that is tapered along a portion of the length of the shank and increases from the tip of shank 51 to a diameter d1 at an intermediate or cylindrical portion 52.

Intermediate portion 52 extends between shank 51 and a head 54 of screw 50. The threads on shank 51 extend into portion 52 by a thread run out 53. According to standard machining practices, cylindrical portion 52 includes a short segment that does not bear any threads. This segment of cylindrical portion 52 interfaces or contacts with a plate thickness at hole 34 or slot 32, 35 through which bone screw 50 extends. This short segment has an outer diameter d1. The head 54 of screw 50 includes a tool recess 55 configured to receive a driving tool. In one specific embodiment, tool recess 55 is a hex recess, or in the alternative, any type of drive recess as would occur to those skilled in the art. Head 54 includes a truncated or flattened top surface 56 having a diameter d4. A spherical surface 57 extends from cylindrical portion 52 to a shoulder 59. Shoulder portion 59 has a diameter d5. An inclined surface 58 extends between shoulder 59 and truncated top surface 56. Inclined surface 58 forms an angle $A_I$ with top surface 56.

It is contemplated that screw 50 may be provided with shank 51 having a length that varies from about 10 mm to about 24 mm. In one specific embodiment of screw 50, the threads have diameter d2 of about 4.5 mm. In another specific embodiment, the diameter d2 is about 4.0 mm. In both specific embodiments, cylindrical portion 52 has a diameter d1 of about 4.05 mm. Cylindrical portion 52 has an unthreaded segment with a height h1 that is determined by standard machining practices for thread run-out between a shank and screw head. Height h1 and diameter d1 of cylindrical portion 52 are sized to achieve a snug fit between screw 50 and plate 31 in hole 34 or slot 32, 35 through which screw 50 is placed. Head 54 is provided with height h2, outer diameter d5 at shoulder 59, diameter d4 at top surface 56, and inclined surface 54 angle $A_I$ such that the head 54 is nested within its corresponding slot 32, 35 or hole 34 and recessed below the top surface of the plate. Although reference has been made to specific dimensions in this specific embodiment, it should be understood that the present invention also contemplates other dimensions and configurations for screw 50. It should also be understood that bone screws used to secure plate 31 can each have a different length and diameters associated therewith, and need not correspond exactly to the other bone engaging fasteners used in the construct.

Figure 7:
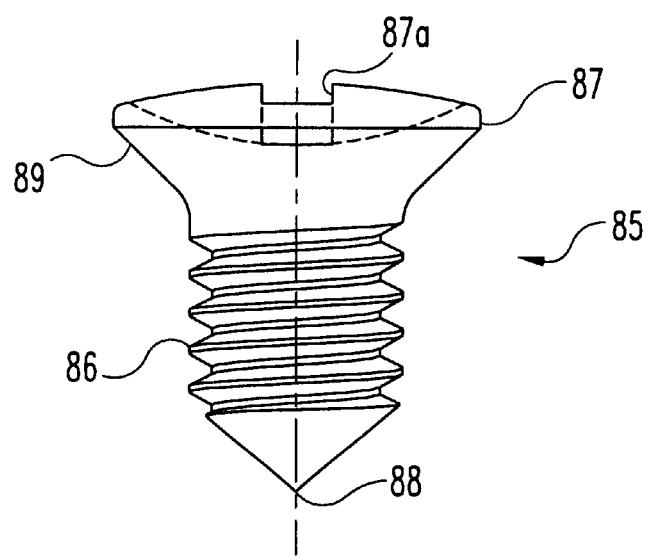
FIG. 7 is a side elevational view of a locking fastener according to another aspect of the present invention.

The details of locking screw 85 are provided in FIG. 7. Locking screw 85 includes a shank 86 having machine threads thereon. In one specific embodiment, locking screw 85 terminates in a sharp point 88 that permits penetration into the vertebral body when locking screw 85 is secured in threaded fastener bore 70. Head 87 includes a lower conical surface 89 configured to mate with aperture 91 of washer 90. Head 87 further includes a tool recess 87a for receiving a driving tool therein.

Further details and embodiments of washer 90 of retainer assembly 33 are provided in FIGS. 8(a)–8(k). Washer 90 includes second body portion 95, first body portion 93, and if necessary, one or more intermediate body portions 94. A connecting portion 98 extends between and connects each of the body portions 93, 94, 95. Washer 90 has a top surface 100a and a bottom surface 100b. Each body portion 94, 95 defines an aperture 91 extending between top surface 100a and bottom surface 100b. Aperture 91 has a tapered countersink portion 92 therearound adjacent top surface 100b. Aperture 91 allows passage of shank 86 of locking screw 85 therethrough, and countersink 92 is preferably configured to mate with conical surface 89 and seat locking screw 85 at various positions along the length of aperture 91. Preferably, countersink portion 92 is sloped toward bottom surface 100b from second end 97 to first end 96. The mating conical features between locking screw 85 and aperture 91 provide a self-translating capability for washer 90 relative to plate 31 as locking screw 85 is tightened into fastener bore 70 of plate 31.

Body portions 93, 94, 95 have a width W1 that is greater than a width W2 of connecting portion 98. The width W1 and length of body portions 93, 94, 95 are configured so that the body portions overlap with recess 45 of holes 34 and recesses 46, 47 of slots 32, 35. The body portions 93, 94, 95 retain the heads of bone screws extending through the holes and slots of plate 31 when washer 90 resides in groove 39 and is in the locked condition of FIG. 2. The width W2 and the length of the connecting portions 98 are configured to allow insertion of screws in holes 34 and slots 32, 35 when washer 90 is in the unlocked condition of FIG. 1.

Figure 8A:
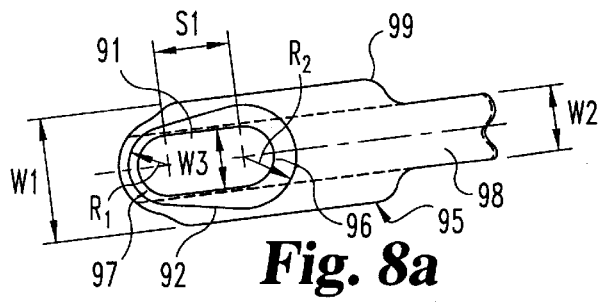
FIGS. 8(a)–8(k) are various views and sections of washers according to the present invention.
Figure 8B:
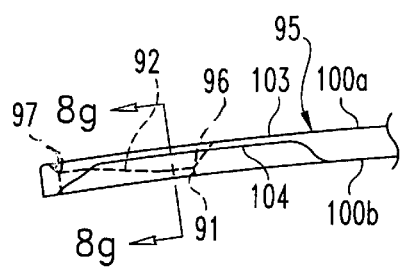

In FIGS. 8(a) and 8(b) there is shown second body portion 95 of washer 90. Aperture 91 has countersink portion 92 that is tapered along the length of aperture 91. Aperture 91 has a width W3 at bottom surface 100b of washer 90. Countersink portion 92 has a width that varies along the length of aperture 91 and is greater than width W3. Countersink portion 92 has a radius R1 at second end 97 and a radius R2 at first end 96 at top surface 100a. It is preferred that R1 is less than R2 and the width of countersink portion 92 increases from second end 97 towards first end 96. Aperture 91 has a chord length S1 extending between the center of radius R1 and the center of radius R2. Body portion 95 further includes a transition portion 99 that extends between connecting portion 98 and body portion 95.

Figure 8C:
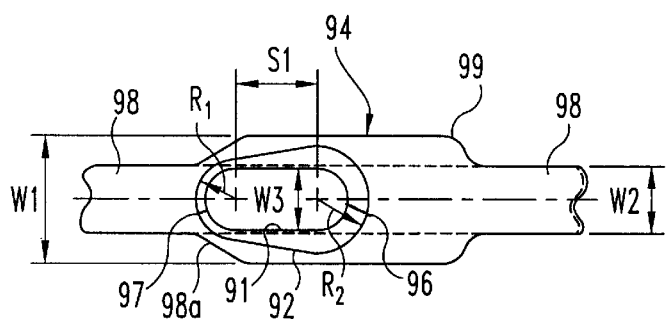
Figure 8D:
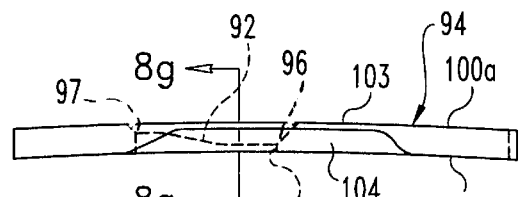

Intermediate body portion 94 of FIGS. 8(c) and 8(d) is similar in many respects to second body portion 95 of FIGS. 8(a) and 8(b), and also includes an aperture 91 having a tapered countersink portion 92. However, intermediate body portion 94 has a connecting portion 98 extending in both directions therefrom. A second transition portion 98a extends between second connecting portion 98 and body portion 94. Body portion 94 has a chord length S1 between the center of radius R1 and the center of radius R2.

Tapered countersink 92 of aperture 91 provides a self-translating capability of the washer 90. This is because the washer 90 is translated relative to plate 31 as the locking screw 85 is threaded into threaded bore 70. The camming conical surface 89 of screw 85 advances downward along the tapered portion of the wall of countersink portion 92 of aperture 91.

Figure 8E:
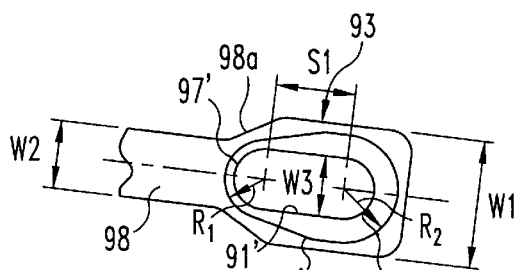
Figure 8F:
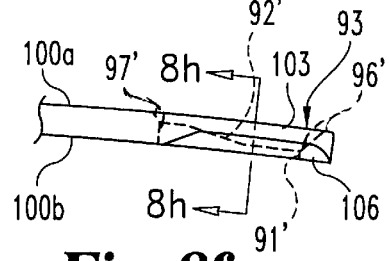

FIGS. 8(e) and 8(f) show first body portion 93. First body portion 93 is also similar to second body portion 95. However, in one embodiment, first body portion 93 includes an aperture 91' having a countersink portion 92' that is not tapered along its length to provide a self-translating capability for washer 90 like the countersink portions 92 of body portions 94 and 95. Rather, after washer 90 is translated relative to plate 31 as described above, locking screw 85 will already be positioned at first end 96', and may thereafter be threaded into bore 70 and seated within countersink portion 92'. Alternatively, the surgeon may slide the washer by hand or with a tool to its translated position, and lock the washer in its translated position by seating locking screw 85 into countersink 92' at first end 96'. Countersink 92' has a definite location at second end 96' for seating locking screw 85, providing a reference for the surgeon to confirm that washer 90 has been translated to its locked position. It should be understood, however, that it is also contemplated herein that body portion 93 could also be provided with aperture 91 like body portions 94 and 95 as shown in FIGS. 1–3.

Figure 8G:
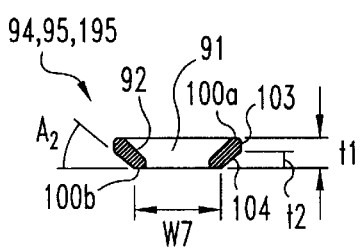

Referring now to FIG. 8(g), a cross-sectional view of washer 90 is provided through aperture 91 of body portion 94, 95. Washer 90 has an outer surface 104 configured to overlap bone screws 50 in slots 32, 35 without contacting inclined surface 58 of screws 50 when retainer assembly 33 is in its locked condition. Outer surface 104 extends from bottom surface 100b to a shoulder 103. Shoulder 103 extends between inclined surface 104 and top surface 100a. Inclined surface 104 forms an angle $A_2$ with respect to bottom surface 100b. Washer 90 defines a thickness t1 between top surface 100a and bottom surface 100b, and a shoulder height of t2 from bottom surface 100b. Washer 90 has a width W7 along bottom surface 100b at aperture 91.

Figure 8H:
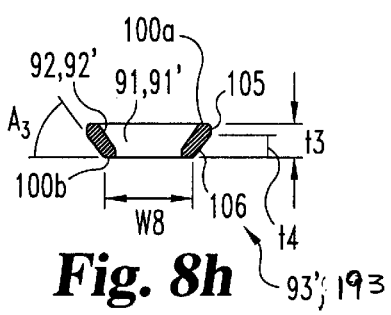

Referring now to FIG. 8(h), a cross-sectional view of washer 90 is provided through aperture 91 or 91' of body portion 93. Washer 90 has contact surface 106 configured to contact inclined surface 58 of screws 50 when retainer assembly 33 is in its locked condition. Contact surface 106 extends from bottom surface 100b to a shoulder 105. Shoulder 105 extends between contact surface 106 and top surface 100a. Contact surface 106 forms an angle $A_3$ with respect to bottom surface 100b that is configured to mate with and provide surface contact with inclined surface 58 of bone screw 50. Washer 90 defines a thickness t3 between top surface 100a and bottom surface 100b, and a shoulder height of t4 from bottom surface 100b.

In one specific embodiment of the washer 90, the body portions have a width W1 and connecting portion have width W2 that is based on the spacing between the centerlines of the paired slots and holes of the plates and the overall width of the plate. The width W3 of aperture 91 in the specific embodiment is sized to accommodate the shank 86 of locking screw 85 without head 87 passing therethrough. The length of body portions 94 and 95 varies based on the length and spacing between slots 32, 35 and holes 34 in plate 31. Preferably, the body portions 94, 95 have a length sufficient to overlap substantially the entire length of slot 32, 35 when retainer assembly 33 is in its locked position. The tapered countersink portion 92 of aperture 91 has radius R1 that transitions to radius R2 along the chord length S1. Thickness t1 is less than thickness t3, and shoulder height t4 is less than shoulder height t2. Body portion 93 has a width W8 along bottom surface 100b that is greater than width W7 of body portions 94, 95. Angle $A_2$ is preferably less that angle A1. The dimensions of washer 90 are preferably arranged so that body portions 94, 95 do not contact the screw heads nested in slots 32, 35 to facilitate translation of the screws in slots 32, 35. Body portion 93 contacts the screw heads nested in holes 34 to further enhance the fixed orientation between screws 50 and plate 31 in holes 34. Although reference has been made to the dimensional attributes of this specific embodiment, it should be understood that the present invention also contemplates other orientations and dimensional relationships for washer 90.

Figure 8I:
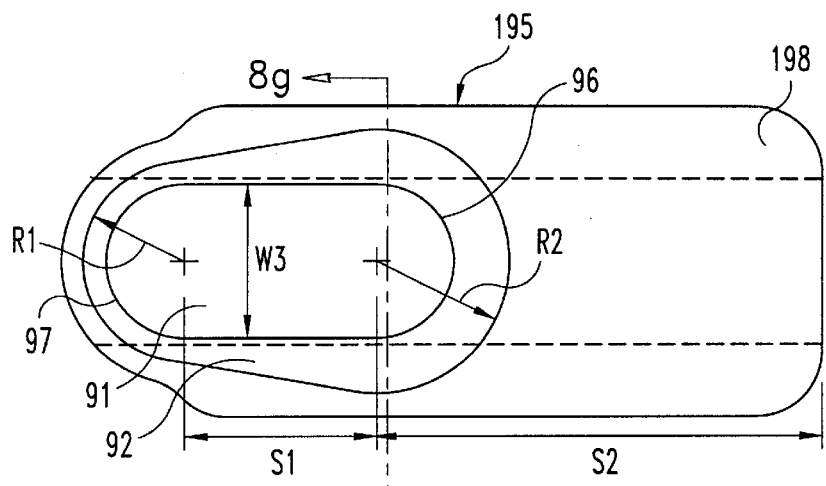
Figure 8J:
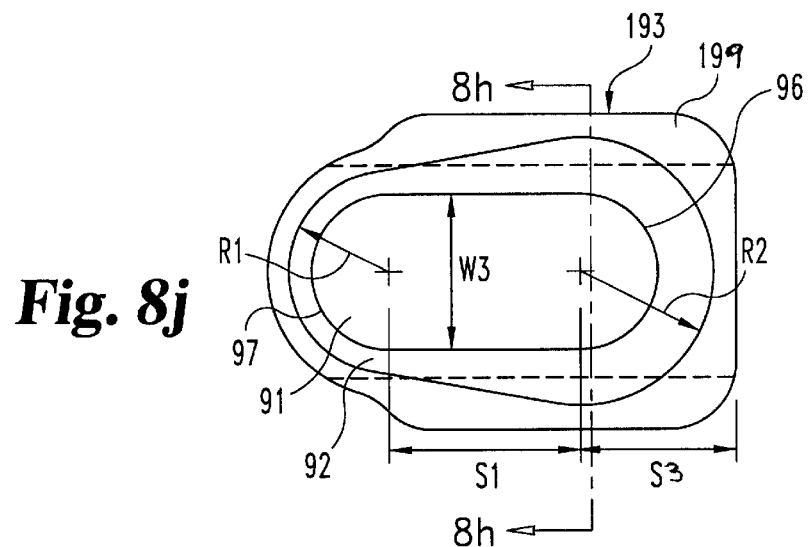

The present invention also contemplates a retainer assembly in which individual washers are provided at each node for retaining screws in holes 34 and slots 32, 35 of plate 31. Referring now to FIGS. 8(i) and 8(j), a slot washer 195 and a hole washer 193 are provided. Slot washer 195 is similar to body portion 95 of washer 90 and hole washer 193 is similar to body portion 93 of washer 90, both of which are described above. Elements that are alike bear the same reference number as the corresponding element of body portions 95, 93. Slot washer 195 and hole washer 193 do not have a connecting portion 98 extending to another washer. Slot washer 195 has a body portion 198 with a length S2 that varies and is sized to correspond to the length of the adjacent slot 32, 35 when washers 195 are positioned on plate 31. Slot washer 195 does not have a connecting portion 98 extending to another washer. Hole washer 193 has a body portion 199 with a length S3 that varies and is sized to correspond to the length of the plate adjacent hole 34 when washer is positioned on plate 31.

Figure 8K:
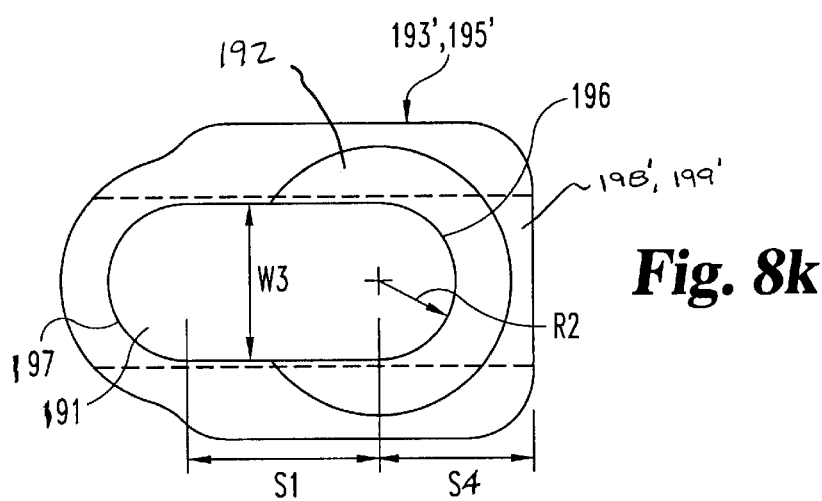

In FIG. 8(k) an alternate embodiment of washers 193 and 195 is provided and designated at 193', 195' respectively. Washers 193', 195' are the same as washers 193, 195 described above, except for aperture 191. Aperture 191 does not have a tapered countersink, but rather has a semi-circular countersink portion 192 only at first end 196. Countersink portion 192 provides a single position for locking screw 85 to lock the washer 193', 195' to plate 31 after the washer 193', 195' has been translated relative to plate 31 by the surgeon. Washers 193', 195' have body portion 198',199' with length S4 that varies as described above with respect to length S2 and S3.

Figure 9:
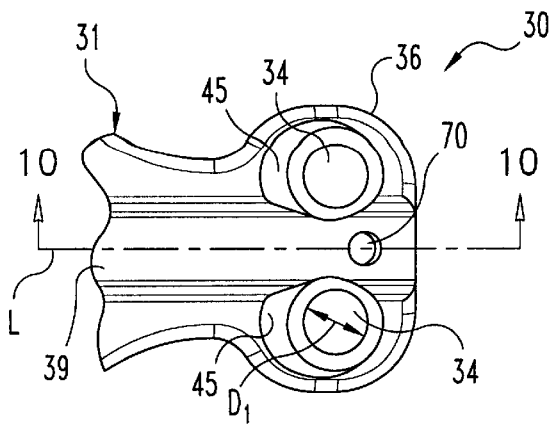
FIG. 9 is a top plan view of a first end of the fixation plate of the present invention.
Figure 10:
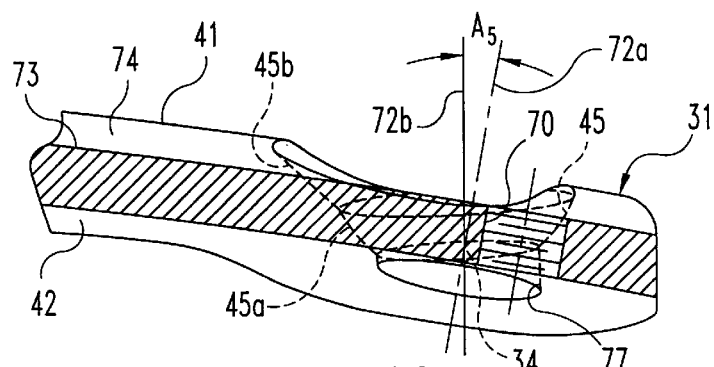
FIG. 10 is a cross-sectional view taken through line 10—10 of FIG. 9.
Figure 11:
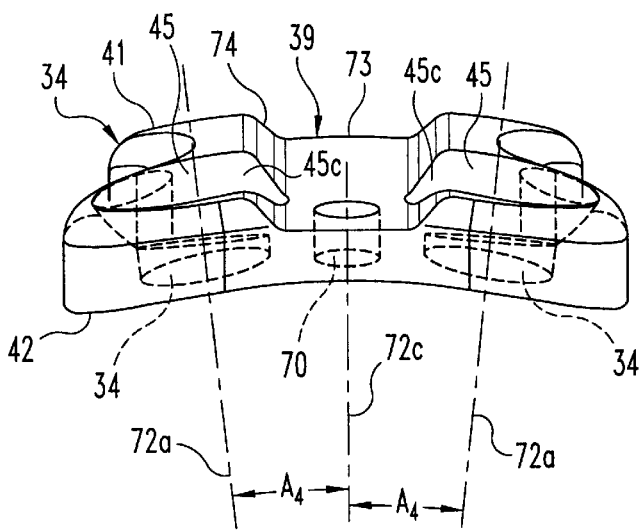
FIG. 11 is an end elevational view of the plate of FIG. 9.

Referring now to FIGS. 9–18, further details of plate 31 will be discussed with reference to illustrations of first node 36, second node 37, and intermediate node 38. In FIGS. 9–11, first node 36 of plate 31 is depicted. It is preferred that holes 34 are identical and symmetrical about axis L. Hole 34 includes recess 45 adjacent top surface 41. Holes 34 include a cylindrical bore 77 having generally vertical sidewalls adjacent bottom surface 42. Cylindrical bore 77 extends between recess 45 and bottom surface 42 of plate 31, and has a diameter D1. Cylindrical bore 77 has axis 72b that is offset at angle $A_5$ from an axis 72a that extends normal to plate 31 as shown in FIG. 10. Recess 45 has a partial spherical portion 45a defined about a central axis 72b. Axis 72b is offset from axis 72a by angle $A_5$. Offset angle $A_5$ directs bone screws inserted into holes 34 toward the first end of plate 31. Furthermore, as shown in FIG. 11, axes 72a converge below the bottom surface 42 of plate 31 at angle $A_4$ with respect to an axis 72c that extends along the centerline of plate 31 perpendicular to axis L. Recess 45 intersects groove 39 at intersecting portion 45c. Spherical portion 45a is configured to mate with spherical surface 57 of bone screw 50, allowing at least a portion of head 54 to be recessed below top surface 41 of plate 31.

To facilitate insertion of drill guides, drills and the bone screws 50, recess 45 also includes a flared portion 45b that extends in a superior direction from axis 72b. In one embodiment, recess 45 includes a wall that parallels bore 77 and extends between between spherical portion 45a and flared portion 45b to further facilitate insertion and maintenance of a drill guide in recess 45.

In one specific embodiment, spherical portion 45a has a diameter that mates with the diameter of spherical surface 57 of screw 50, and is slightly larger than diameter d5 of head 54 of bone screw 50. The cylindrical bore 77 of hole 34 has a diameter D1 of 4.1 mm, which is slightly larger than the diameter d1 of intermediate portion 52 of screw 50. This portion of the screw contacts bore 77 and assumes a fixed orientation with respect to plate 31. In this specific embodiment, offset angle $A_5$ is about 12.6 degrees and convergence angle $A_4$ is about 6 degrees relative to axis 72c. Although reference has been made to the dimensional attributes of this specific embodiment, it should be understood that the present invention also contemplates other dimensions.

Figure 12:
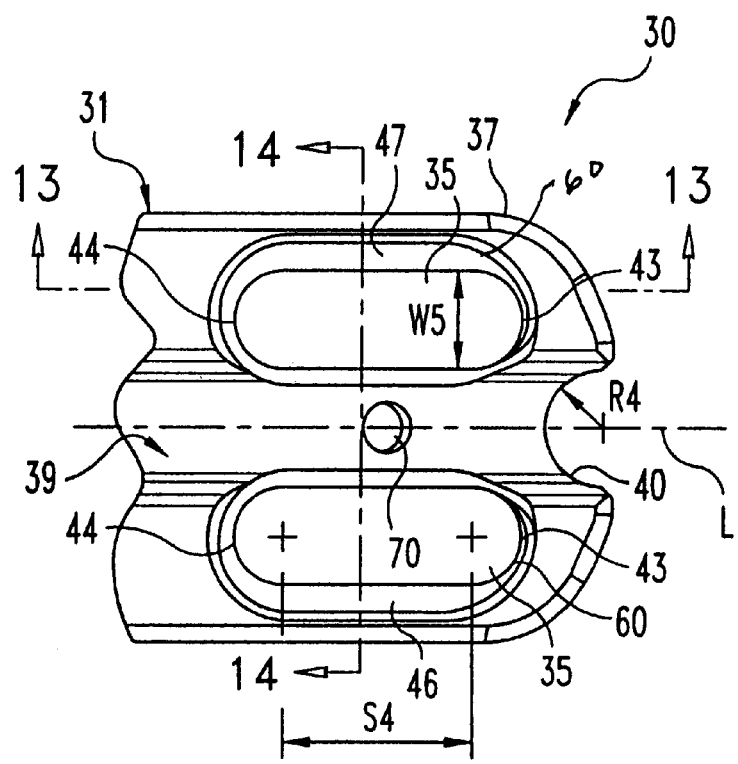
FIG. 12 is a top plan view of a second end of the fixation plate of the present invention.
Figure 13:
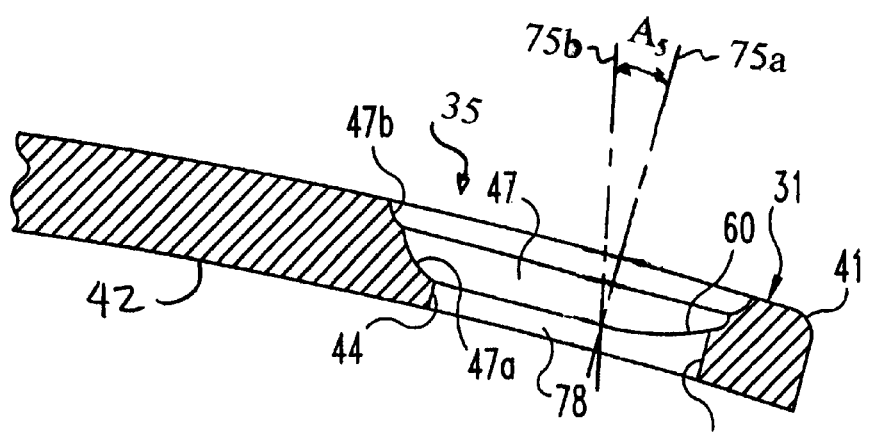
FIG. 13 is a cross-sectional view taken along line 13—13 of FIG. 12.
Figure 14:
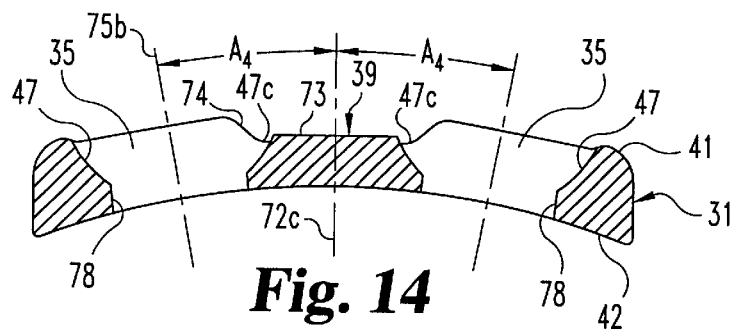
FIG. 14 is an enlarged cross-sectional view taken through line 14—14 of FIG. 12.

Referring now to FIGS. 12–14, second vertebral node 37 is depicted. Vertebral node 37 includes slots 35 that are preferably identical and symmetrical about axis L. Slot 35 includes slotted bore 78 adjacent bottom surface 42 of plate 31 having generally vertical sidewalls extending between second end 43 and first end 44. Slotted bore 78 extends between bottom surface 42 and recess 47 adjacent top surface 42. Bore 78 has a width W5 and a chord length S4, and has a central axis 75b extending through plate 31. Recess 47 has a spherical portion 47a about central axis 75b that extends around slot 35. As shown in FIG. 13, central axis 75b is offset from axis 75a that extends normal to plate 31 by angle $A_5$. Offset angle $A_5$ directs bone screws inserted into slot 35 towards the second end of plate 31. It should be noted that slot 35 allows insertion of a bone screw at angles less than $A_5$ in slot 35, and bone screw 50 may be positioned within slot 35 at any location between ends 43 and 44. However, retaining assembly 33 provides for insertion of bone screws 50 at second 43 as would be clinically desirable for settling. Furthermore, as shown in FIG. 14, axes 75b converge below the bottom surface 42 of plate 31 at angle $A_4$ with respect to axis 72c.

Spherical portion 47a is configured to mate with spherical surface 57 of bone screw 50, allowing at least a portion of head 54 to be recessed below top surface 41 of plate 31. To facilitate insertion of drill guides, drills and the bone screws 50, recess 47 also includes a flared portion 47b that extends around spherical portion 47a. In one embodiment, it is contemplated that recess 47 include a wall that parallels bore 78 extending between spherical portion 47a and flared portion 47b to further facilitate maintenance and insertion of a drill guide in recess 47. Recess 47 intersects groove 39 at overlap portion 47c, as shown in FIG. 14. The second end of second node 37 includes notch 40 having radius R4 centered about axis L. It is also contemplated herein that plate 31 is provided without notch 40, as shown in FIGS. 4(a)–4(c).

In a preferred embodiment, slot 35 includes ramp 60 extending between bore 78 and flared portion 47b at second end 43. Ramp 60 is not configured to allow spherical surface 57 of screw 50 to seat therein, but has an orientation that causes second end 43 of slot 35 and screw 50 to separate as screw 50 is threaded into slot 35. Spherical surface 57 of head 54 provides camming action along the ramp 60 until head 54 seats in recess 47 at a position spaced a distance from second end 43. This camming action applies a dynamic compression load to the spinal column portion. The amount of compression applied to the spinal column portion is controlled by the length of ramp 60 from second 43 to the position in slot 35 where screw 50 seats in recess 47. It should be understood that slot 35 may also be provided without ramp 60.

In one specific embodiment, spherical portion 47a has a diameter sized to mate with spherical surface 57 of screw 50, and is slightly larger than diameter d5 of head 54 of bone screw 50. Slotted bore 78 has a width W5 of about 4.1 mm, which is slightly larger than the diameter d1 of intermediate portion 52 of screw 50. The cylindrical portion 52 of bone screw 50 contacts plate 31 in bore 78 and prevents rotation of screw 50 transverse to axis 72c. The chord length S4 varies depending upon the length of the slot 35 needed for the particular application of plate 31 and patient anatomy. In this specific embodiment, offset angle $A_5$ is about 12.6 degrees and convergence angle $A_4$ is about 6 degrees relative to an axis 72c. Although reference has been made to the dimensional attributes of this specific embodiment, it should be understood that the present invention also contemplates other dimensions.

Figure 15:
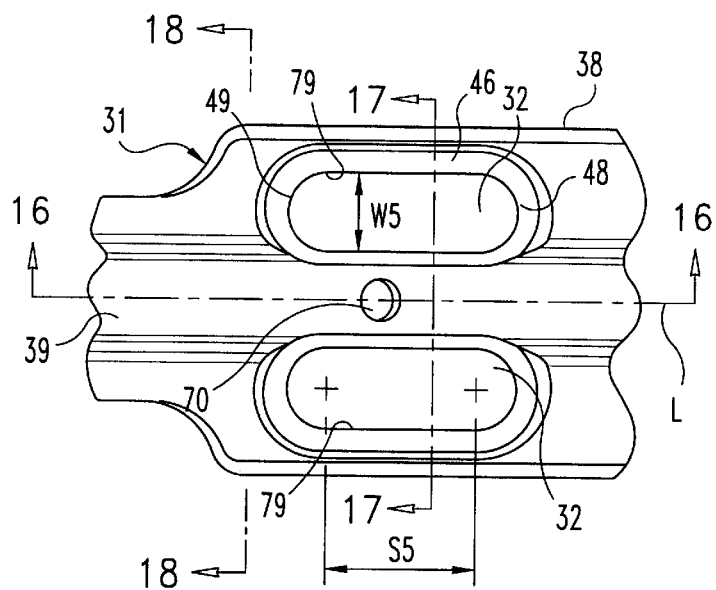
FIG. 15 is a top plan view of an intermediate portion of the fixation plate of the present invention.
Figure 16:
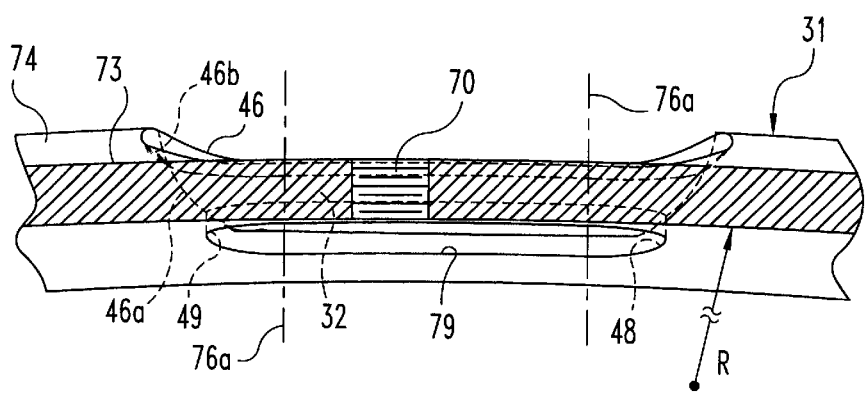
FIG. 16 is a cross-sectional view taken through line 16—16 of FIG. 15.
Figure 17:
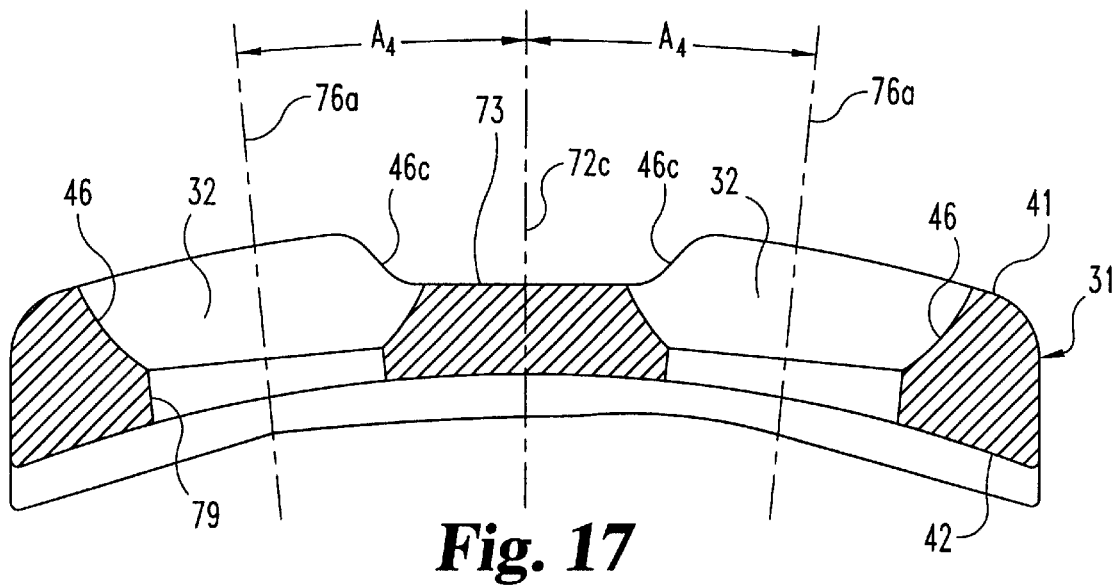
FIG. 17 is an enlarged cross-sectional view taken through line 17—17 of FIG. 15.

Referring now to FIGS. 15–17, various views of intermediate node 38 are depicted. Vertebral node 38 includes slots 32 that are preferably identical and symmetrical about axis L. Slot 32 includes slotted bore 79 adjacent bottom surface 42 of plate 31 having generally vertical sidewalls extending between a second end 48 and a first end 49. Slotted bore 79 extends between bottom surface 42 and recess 46 adjacent top surface 42. Bore 79 has a width W5 and a chord length S5, and has a central axis 76a extending through plate 31. Recess 46 has a spherical portion 46a that extends around slot 35. As shown in FIG. 16, central axis 76a generally extends normal to plate 31. However, as shown in FIG. 17, the axes 76a converge below the bottom surface 42 of plate 31 at angle $A_4$ with respect to axis 72c. It should be noted that slot 32 allows insertion of bone screws 50 at various angles with respect to axis 76a.

Spherical portion 46a is configured to mate with spherical surface 57 of bone screw 50, allowing at least a portion of head 54 to be recessed below top surface 41 of plate 31. To facilitate insertion of drill guides, drills and bone screws 50, recess 46 also includes a flared portion 46b that extends around spherical portion 46a. In one embodiment, a wall paralleling bore 79 extends between spherical portion 46a and flared portion 46b to further facilitate insertion and maintenance of a drill guide in recess 46. Screw 50 may be placed within intermediate slot 32 between ends 48 and 49. However, it is preferred that the screw is inserted initially at second end 48, thus allowing compression loading of the spinal column segment. Recess 46 intersects groove 39 at overlap portion 46c, as shown in FIG. 17.

In one specific embodiment, spherical portion 46a has a diameter sized to mate with spherical surface 57 of screw 50, and is slightly larger than diameter d5 of head 54 of bone screw 50. The slotted bore 79 has a width W5 of about 4.1 mm, which is slightly larger than the diameter d1 of intermediate portion 52 of screw 50. Cylindrical portion 52 of bone screw 50 interfaces with plate 31 in bore 79 such that angular adjustment of screw 50 transverse to axis 72c is prevented. The chord length S5 varies depending upon the length of slot 35 needed for the particular application of plate 31 and patient anatomy. In this specific embodiment, convergence angle $A_4$ is about 6 degrees relative to an axis 72c. Although reference has been made to the dimensional attributes of this specific embodiment, it should be understood that the present invention also contemplates other dimensions.

Figure 18:
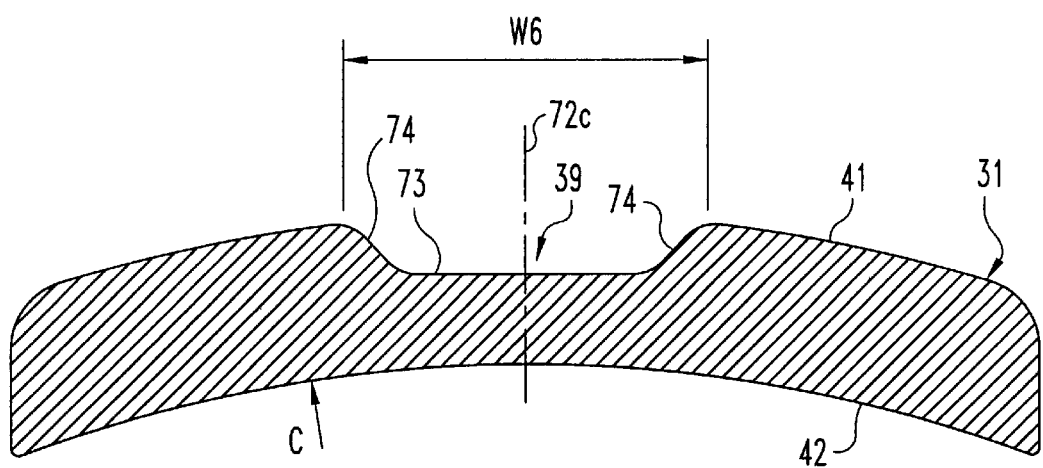
FIG. 18 is an enlarged cross-sectional view taken through line 18—18 of FIG. 15.

Referring now to FIG. 18, a cross-sectional view of plate 31 is provided through line 18—18 of FIG. 15. Groove 39 has a width W6 at top surface 41 of plate 31. Groove 39 has bottom surface 73 extending between inclined sidewalls 74. Sidewalls 74 extend between bottom surface 73 of groove 39 and top surface 41 of plate 31. It is contemplated that the groove 39 has a depth sufficient to accommodate the washer 90 so as to minimize protrusion of washer 90 above top surface 41 of plate 31.

To accommodate the anterior application of the fixation plate assembly 30, the plate is curved in two degrees of freedom. Specifically, the bottom surface 42 of the plate can be curved along a large radius R, centered in a vertebral plane containing central axis L, as shown schematically in FIG. 16, to accommodate the lordotic curvature of the cervical spine. In addition, bottom surface 42 forms a medial/lateral curvature C, as shown in FIG. 18, to correspond to the curvature of the vertebral body. It is understood that plate 31 can also be bent as needed to accommodate the particular spinal anatomy and vertebral pathology.

Figure 19A:
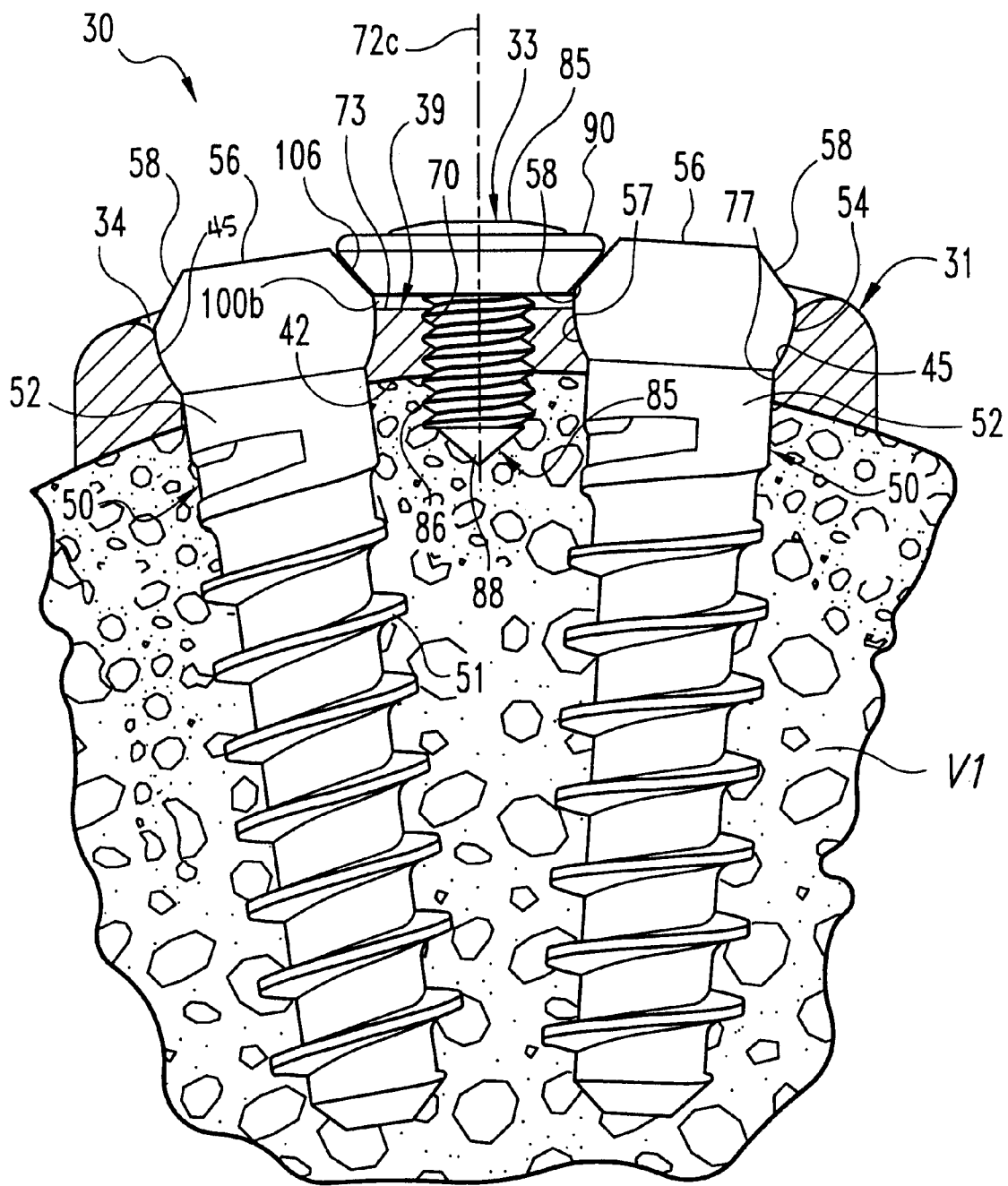
FIG. 19a is a partial sectional view of the anterior plate assembly of the present invention with the screws disposed through the holes at the first end of the plate and engaged in a vertebra.

Referring now to FIG. 19a, a partial sectional view of fixation plate assembly 30 at holes 34 is provided with screws 50 engaged to vertebra V1 and retainer assembly 33 in the locked position. A pair of screws 50 are disposed within the respective holes 34 so that the threaded shanks 51 project beyond the lower surface 42 of plate 31 into the vertebral body V1. The intermediate portion 52 of screw 50 extends through the bore 77 of the hole 34. Spherical surface 57 of head 54 contacts recess 45 of hole 34 when screw 50 is seated therein. The intermediate portion 52 provides a snug fit for screw 50 in the bore 77 so that screw 50 is not able to pivot with respect to plate 31.

Figure 19B:
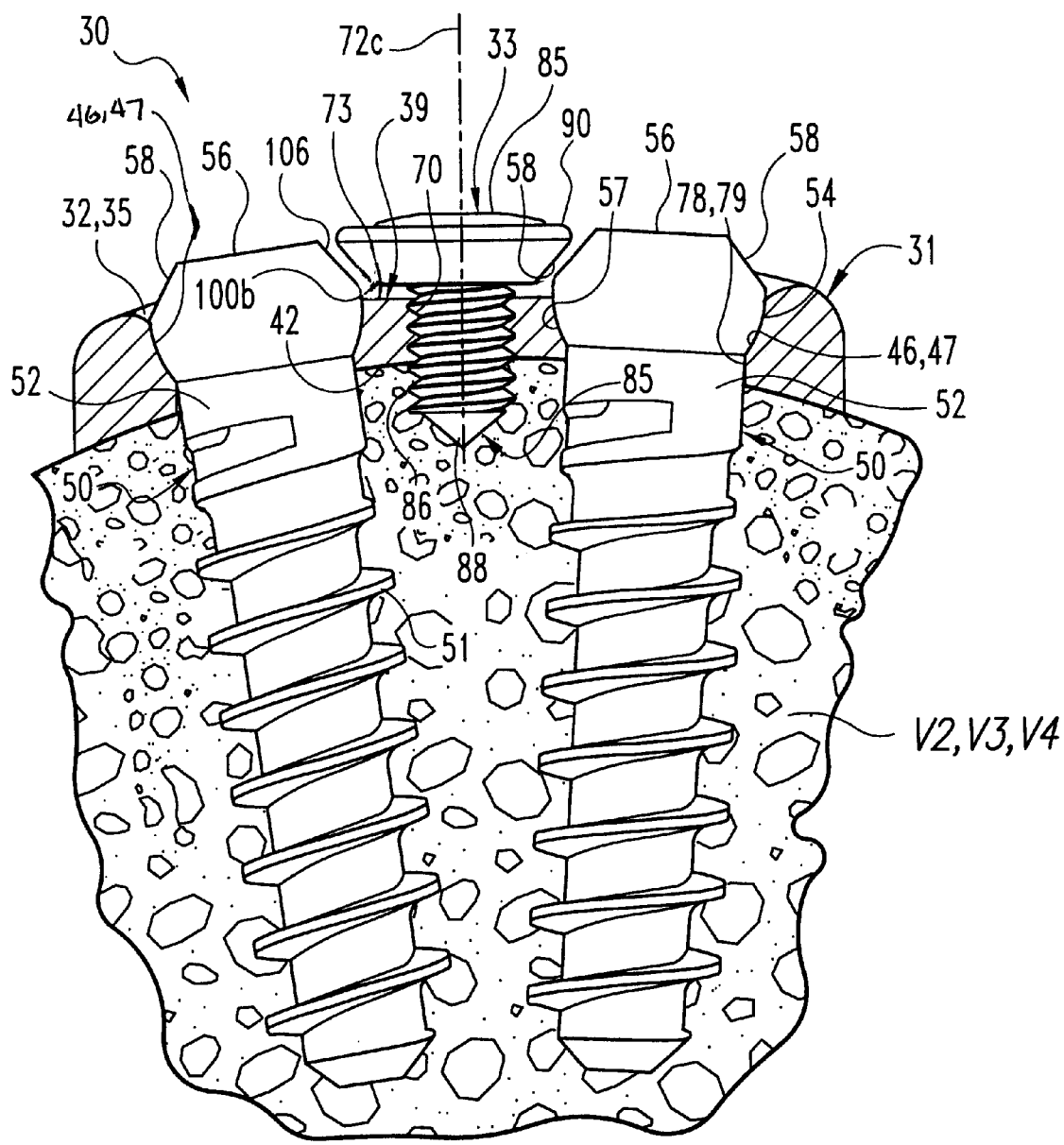
FIG. 19b is a partial sectional view of the anterior plate assembly of the present invention with the screws disposed through the slots of the plate and engaged in a vertebra.

Referring to FIG. 19b, a partial sectional view of fixation plate assembly 30 at slots 32 or 35 is provided with screws 50 engaged to vertebra V1 and retainer assembly 33 in the locked position. A pair of screws 50 are disposed within respective slots 32, 35 so that threaded shanks 51 project beyond lower surface 42 of plate 31 into the corresponding vertebral body V2, V3, or V4. Cylindrical portion 52 of screw 50 extends through bores 78, 79 of slots 35 and 32, respectively. Spherical surface 57 of head 54 contacts recesses 46, 47 of slots 32, 35 when screw 50 is seated therein. Cylindrical portion 52 provides a snug fit for screw 50 in bores 78, 79 so that screw 50 is not able to pivot or translate with respect to axis 72c of plate 31. Of course, screws 50 inserted into slots 32 or 35 are able to translate along the length of slots 32, 35 as described above. It should be understood that the present invention also contemplates various embodiments of plate 31 that use variable angle screws capable of assuming universal angular orientation with respect to plate 31 in slots 32, 35 and holes 34.

In order to ensure screws 50 are retained within plate 31, retainer assembly 33 is moved to its locked position where it contacts the heads 54 of bone screws 50 in holes 34. Locking screw 85 is threaded into threaded fastener bore 70 of plate 31 to translate washer 90 from its unlocked position to its locked position, as described above, and to draw contact surface 106 into contact with inclined surface 58 of screw 50 as shown in FIG. 19a. Contact surface 106 preferably applies a downward force onto head 54 to firmly seat the screw heads within the plate recesses and further fix screw 50 in hole 34. In a preferred embodiment, this downward force is exacted by washer 90 as surface 106 contacts inclined surface 58. As shown in FIG. 19b, outer surface 104 of washer 90 does not contact the heads of bone screws 50 in slots 32, 25. Outer surface 104 overlaps the bone screws 50 to retain bone screws in slots 32, 35. Outer surface 104 will contact the heads of the bone screws if the bone screws backout from slots 32, 35. It is preferred that bottom surface 100b of washer 90 does not contact bottom surface 73 of groove 39.

In a further aspect of the invention, the retainer assembly 33 may be loosely fixed on plate 31 so the surgeon need not fiddle with applying retainer assembly 33 to plate 31 during surgical procedures. The locking fasteners 85 are pre-inserted through apertures 91 of washer 90 and partially threaded into fastener bores 70. Washer 90 is initially positioned such that the second end of each aperture 91 is positioned adjacent locking screw 85. After positioning screws 50 through the holes and slots of plate 31, locking fasteners 85 are advanced further into bores 70 and along tapered portions 92 of apertures 91 to translate washer 90 to a locked condition and retain bone screws 50 in plate 31.

As previously mentioned, sharp point 88 of locking screw 85 is preferably configured to penetrate the cortical bone. In one embodiment, sharp point 88 will penetrate the vertebra when plate 31 is initially positioned on the bone. In this instance, locking screw 85 helps locate and temporarily stabilize the plate on the vertebra as the bone screws 50 are engaged to the vertebra. This temporary location feature provided by locking screw 85 can also be used to maintain the position of plate 31 on the vertebra as a drill guide is used to drill and tap the vertebrae to receive bone screws 50.

According to another aspect of the invention, there are provided instruments and techniques for securing plate 31 to vertebrae of a spinal column segment and for applying a compression load to a graft or implant placed in the spinal column segment. Referring to FIGS. 20(a)–20(f), a guide 150 includes a handle 152, a template 154, and arm 153 extending therebetween. Preferably, arm 153 extends outward from the spine and is bent so that handle 152 parallels the spine, positioning handle 152 out of the way of the surgeon. Template 154 includes a second end 155 that defines a notch 158. Template 154 also includes first end 156 having a projection 156a extending downward therefrom towards vertebral body V2. Template 154 further defines a pair of slots 157 between second end 159 and first end 156.

The surgeon selects a guide 150 with a template 154 sized to position notch 158 at the desired location on vertebra V2 and places guide instrument 150 on vertebral body V2. Notch 158 is located on vertebra V2 by placing projection 156a in abutting contact with the endplate of vertebra V2 in disc space D. Slots 157 provide a visual indication to the surgeon of the range of positions available for screw insertion into the vertebral body through slots 35 of plate 31. If desired, the surgeon can obtain a desired position or location of notch 158 and the desired available range of bone screw positions on vertebra V2 by selecting a guide having a different sized template 154.

Figure 20A:
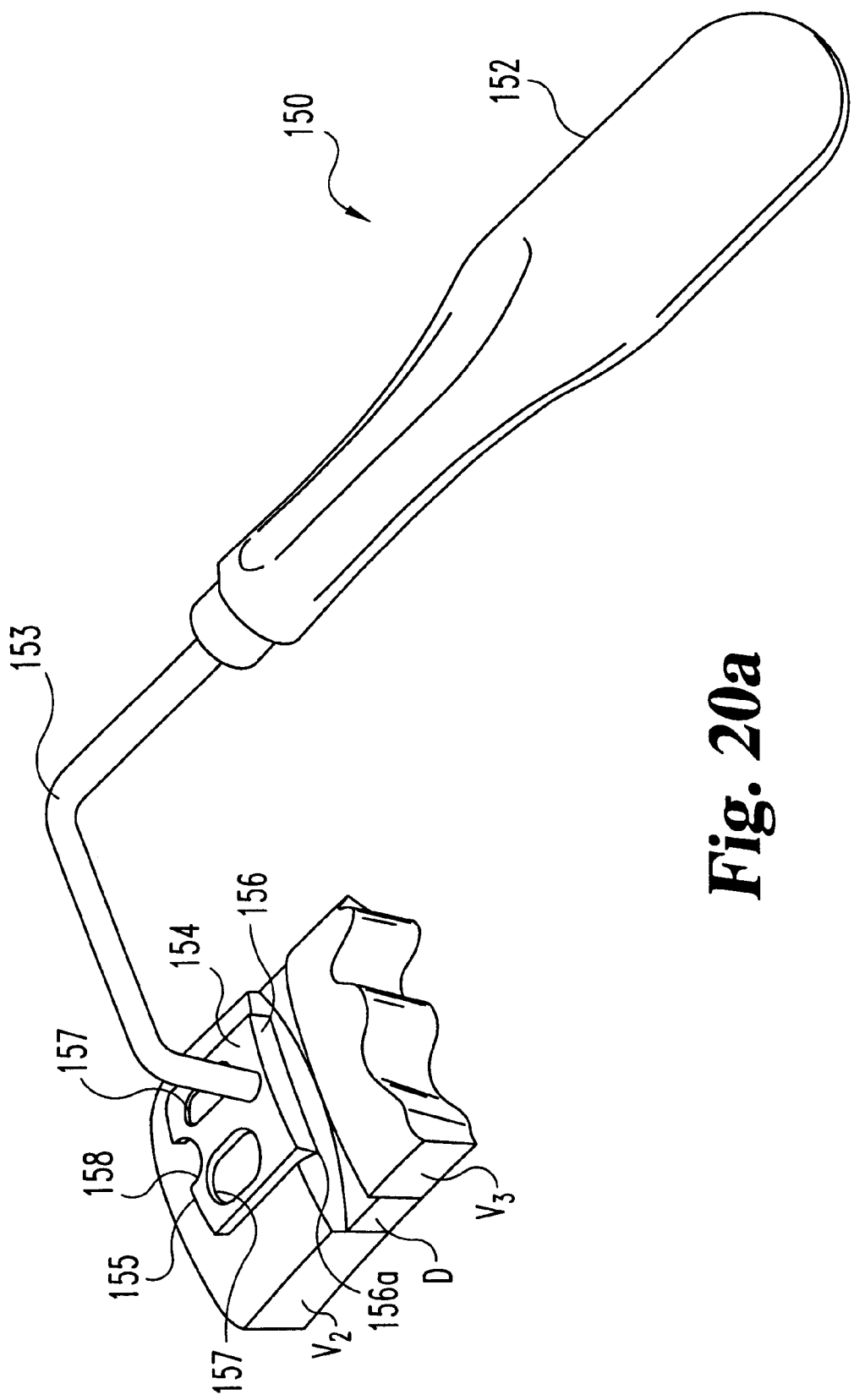
FIGS. 20(a)–20(f) illustrate various instruments and steps of a method according to another aspect to the present invention.
Figure 20B:
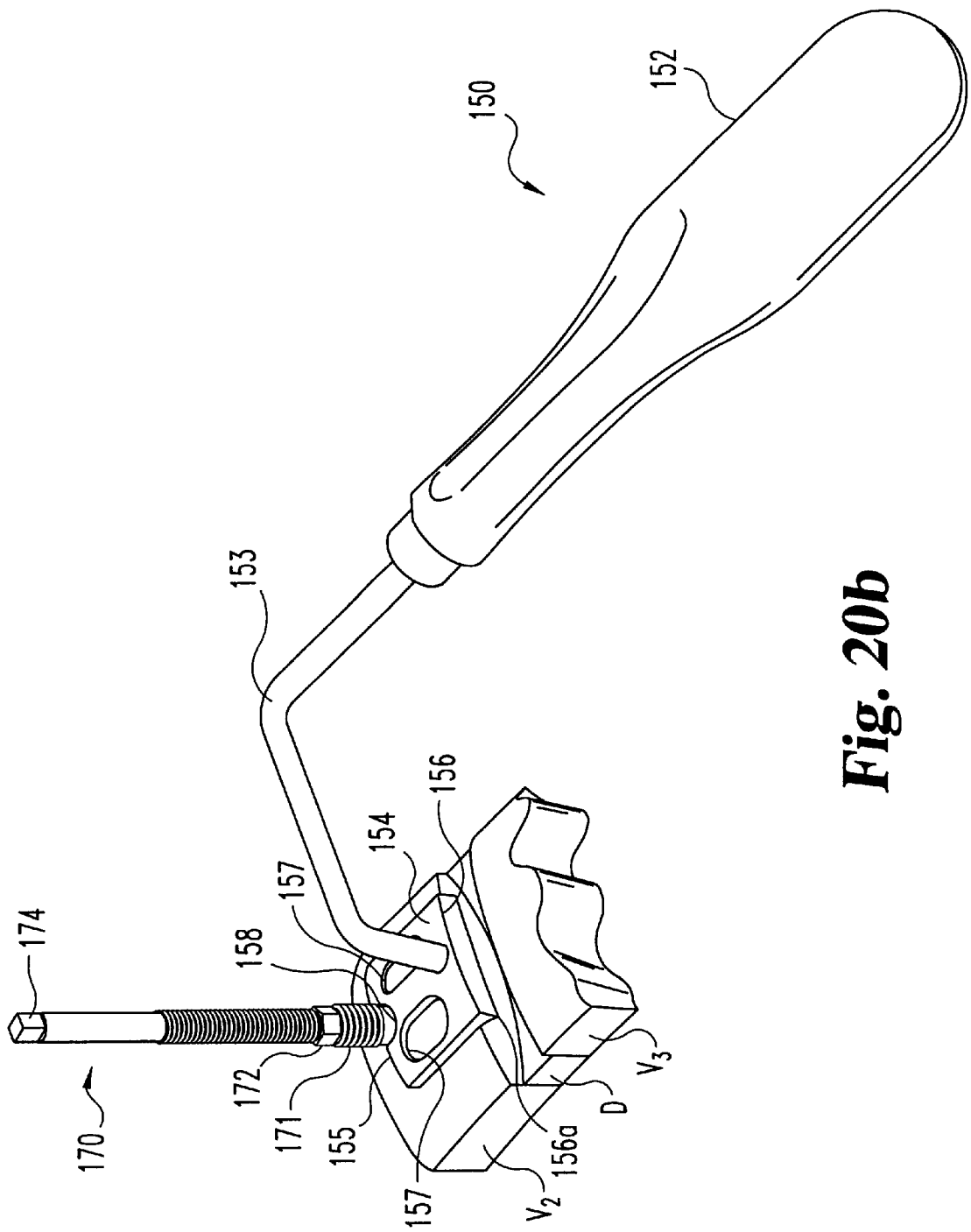

Referring now to FIG. 20(b), after the notch is in the desired position on vertebra V2, a compression pin 170 is placed into vertebra V2 guided by notch 158. Pin 170 includes a lower end 171 having a threaded portion (not shown) for attaching pin 170 to vertebra V2. The attachment portion is preferably threaded to screw into vertebra V2, but may also be smooth with a spiked tip for insertion into the vertebra. Pin 170 also includes tool engagement portion 172 to facilitate installation of pin 170 to the vertebral body. It is also contemplated that the surgeon can place pin 170 on the vertebral body spaced away from notch 158 if desired and the vertebral anatomy so allows.

Figure 20C:
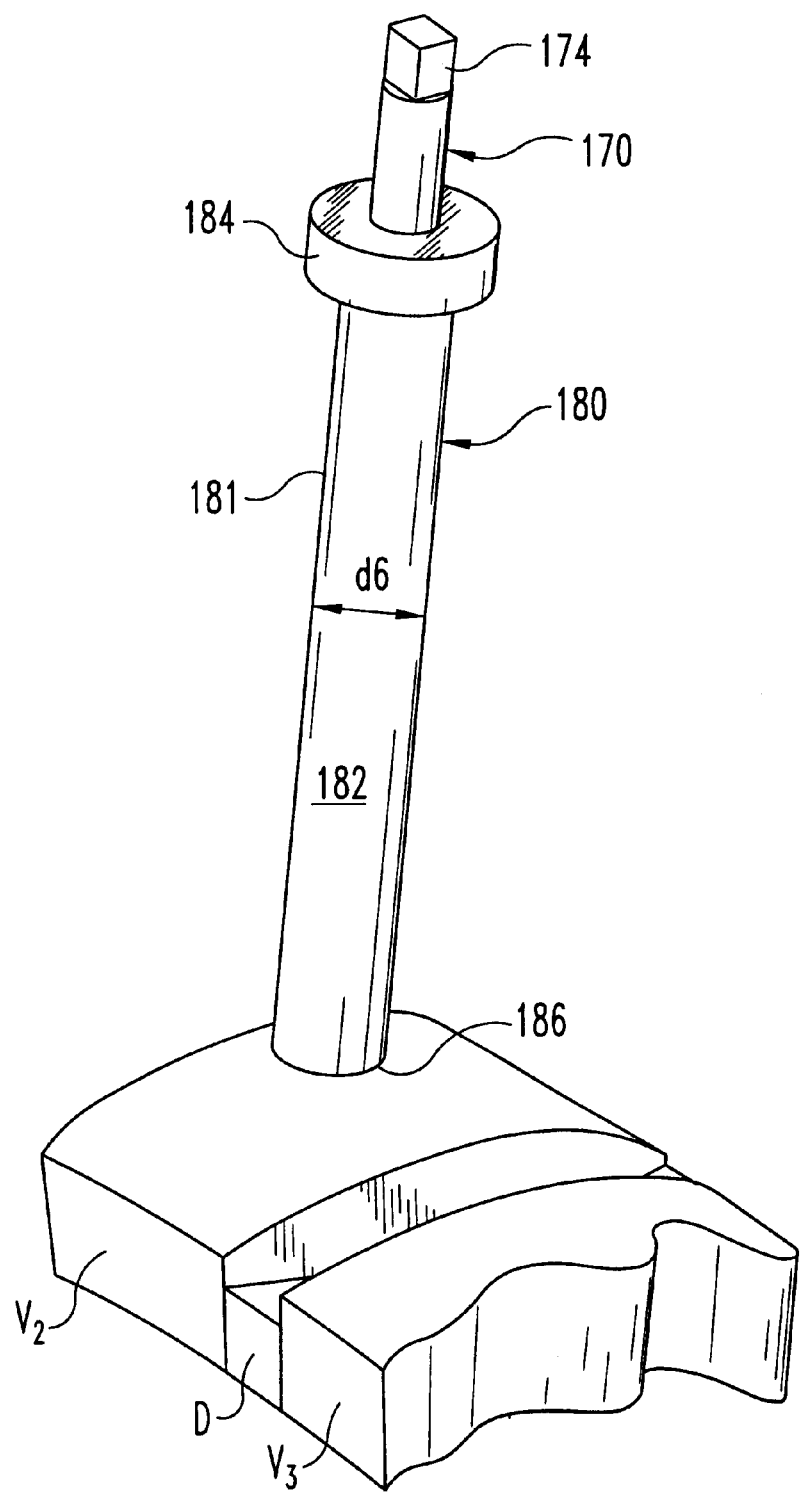

After pin 170 is engaged to vertebra V2, guide 150 is removed and a sleeve 180 is placed over pin 170 as shown in FIG. 20(c). Sleeve 180 has a hollow body 181 extending between a first end 186 adjacent vertebra V1 and a second end 184. A second end 174 of pin 170 preferably extends from second end 184 of sleeve 180, allowing access to pin 170. Sleeve 180 includes enlarged portion 184 to facilitate placement and removal of sleeve 180. It is contemplated that sleeve 180 has hollow interior and an internal configuration that provides secure attachment to pin 170. Body 181 includes cylindrical outer surface 182 with an outer diameter d6.

Figure 20D:
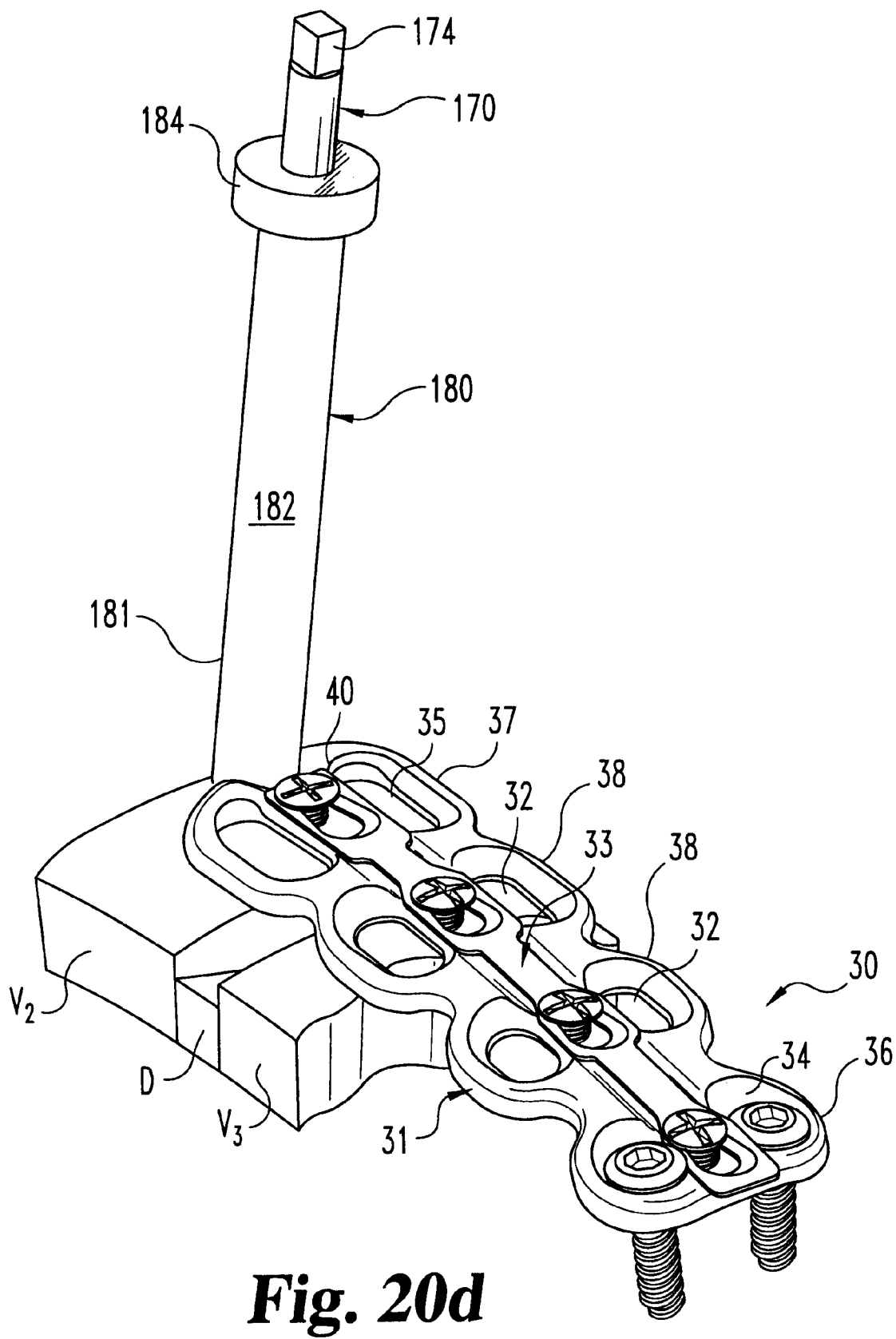

With sleeve 180 in its proper position, plate 31 is positioned with notch 40 in abutting contact with outer surface 182 of sleeve 180, as shown in FIG. 20(d). The diameter d6 of sleeve 180 slightly less than the twice the radius of notch 40 so that notch 40 is nested around sleeve 180. Plate 31 is then secured to vertebra V1 by inserting screws 50 through holes 34.

Figure 20E:
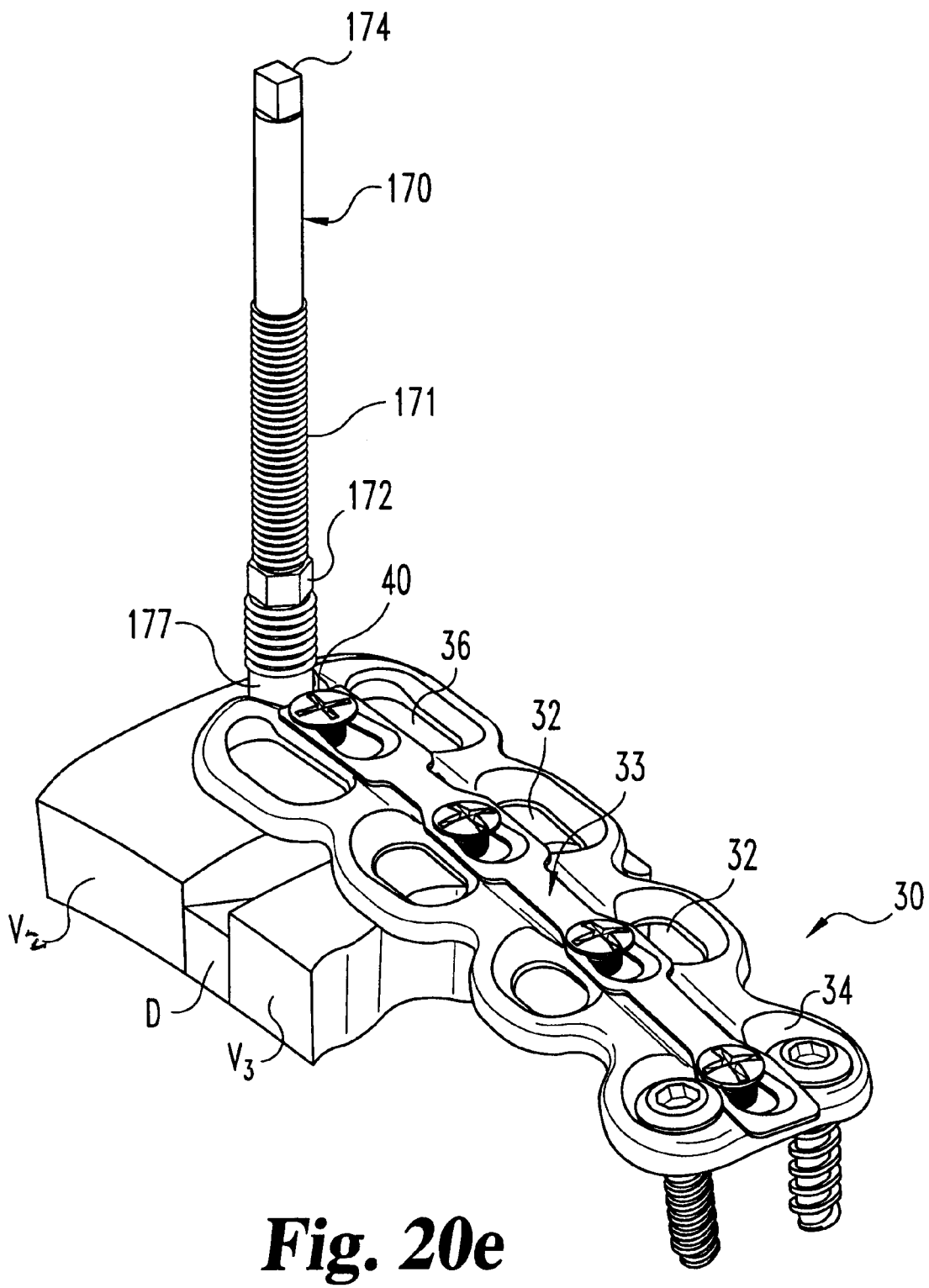

With plate 31 secured to the vertebra V1, sleeve 180 is removed from pin 170, as shown in FIG. 20(e), forming a gap 177 between pin 170 and notch 40. In a preferred embodiment, it is contemplated that gap 177 is about 2 mm. However, other sizes for gap 177 are contemplated herein based on the desired compression to be applied.

Figure 20F:
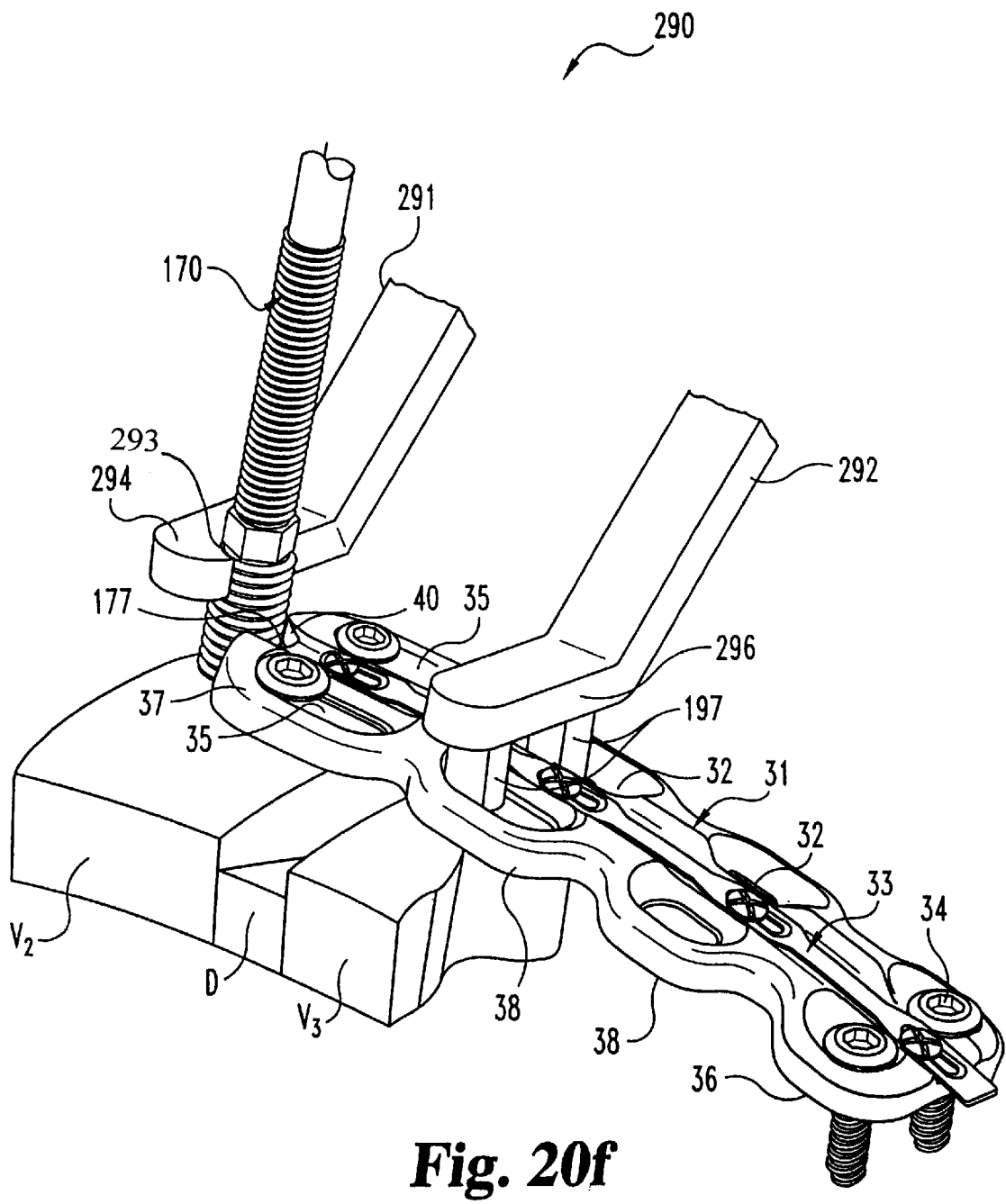

Referring now to FIG. 20(f), a compression tool 290 is secured to pin 170 and to slots 32 of plate 31. It is also contemplated that the compression tool can be secured to plate 31 other than at slots 32 by, for example, engaging the sides of plate 31. Compression tool 290 has a first arm 291 with a first foot 294 connected to pin 170. Second arm 292 is connected to the second end of slots 32 via extensions 297 extending from second foot 296. First arm 291 and second arm 292 are manipulated by the surgeon to apply a compression load to the spinal column segment. The amount of applied load is limited by gap 177 between pin 170 and notch 40. For example, in the specific embodiment where gap 177 is 2 mm, the spinal column portion is compressed 2 mm.

Bone screws 50 are inserted into slots 35 with compression tool 290 maintaining the compression load. With ramp 60 at second 43 of slot 35, an additional amount of dynamic compression is achieved with screw insertion in slots 35, as described above. With screws 50 seated at end 43 of slots 35, compression tool 290 may be removed without release of the compression load. Additional bone screws may be inserted into intermediate slots 32. Washer 90 may then be translated as described above to retain bone screws 50 in plate 31. It should be note that it is contemplated herein that compression tool 290 and pin 170 are preferably only used with plates providing instrumentation at three or more vertebra. However, utilization of a compression tool configured to engage a plate for providing instrumentation at two vertebrae is not precluded.

Figure 21A:
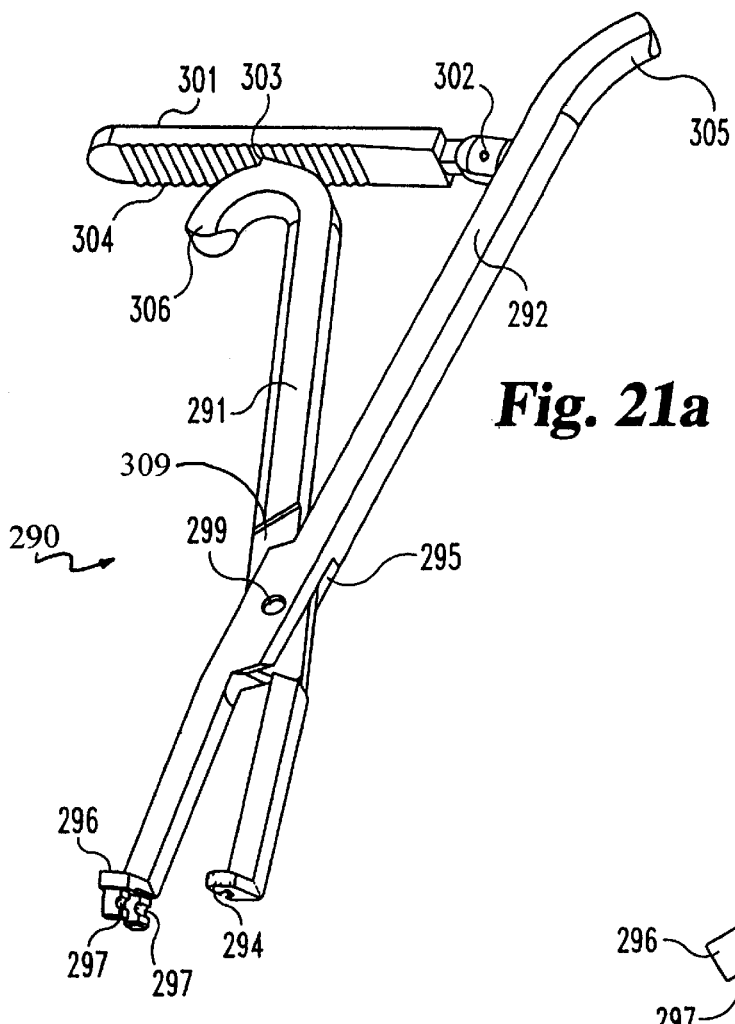
FIGS. 21(a)–21(c) are various perspective views of a compression tool according to yet another aspect of the present invention.
Figure 21B:
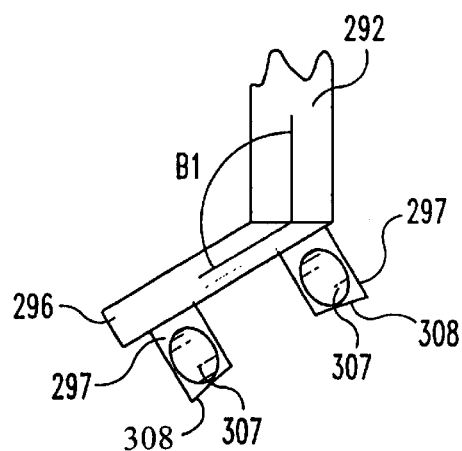
Figure 21C:
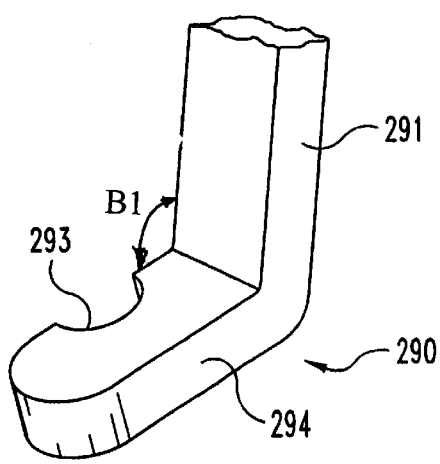

Referring now to FIGS. 21(a)–21(c), further details of compression tool 290 are provided. Tool 290 has first arm 291 having first foot 294 extending therefrom. First foot 294 defines recess 293 for receiving the pin 170. Second arm 292 has second foot 296 extending therefrom. Second foot 296 includes extensions 297 extending downward therefrom configured to engage intermediate slots 32 of plate 31. Extensions 297 preferably include recesses 307 that are configured contact the second ends of intermediate slots 32. It is also contemplated that extensions 297 have a curved bottom surface 308 that corresponds to the medial lateral curvature of the vertebral bodies.

First arm 291 has a reduced thickness portion 299 extending through a passage 295 formed in second arm 292, and is pivotally coupled to second arm 292 with pin 299. First arm 291 has curved handle portion 306 having a projection 303 extending therefrom. Second arm 292 has a handle 305. A ratchet bar 301 is pivotally coupled to second arm 292 via coupling 302. Preferably, ratchet bar 301 is spring-biased towards projection 303. Serrations 304 formed on the bottom side of ratchet mechanism 301 provide for selective engagement with projection 303 on first arm 291.

The first and second arms are compressed towards one another to apply the compressive load to the vertebral segment. Projection 303 engages the serrated bottom of ratchet bar 301 to prevent relaxation of the arms and allows the surgeon to maintain the compression load during insertion of bone screws 50 within slots 35. Ratchet bar 301 may be lifted against its spring bias away from arm 291 to disengage ratchet bar 301 from projection 303. Arms 291, 292 may then be moved away from one another to release compression tool 290 from pin 170 and plate 31.

While compression tool 290 has been illustrated and described in detail, the present invention also contemplates other tools capable of being secured between pin 170 and plate 31 to provide a compression load to the spinal column segment. For example, referring now to FIGS. 22(a) and 22(b), it is contemplated that a compression tool may include one or more angular modifications to first arm 391 and second arm 392 to facilitate access to plate 31 and pin 170 at the surgical site. First arm 391 has a lower portion 391a forming angle B1 with first foot 396. First foot 396 has extensions 397 extending therefrom that are similar to extensions 297 of tool 290. First arm has an upper portion 391c that terminates with curved handle 406. Curved handle 406 has projection 403 extending therefrom to engage a ratchet bar extending from second arm 392. Arm 391 has a vertical extension 391b extending between lower portion 391a and upper portion 391c. Angle B2 is formed between lower portion 391a and vertical portion 391b. Angle B1 is formed between vertical portion 391b and upper portion 391c. Vertical portion 391b as a region of reduced thickness 399 for connection with second arm 392.

Second arm 392 has a lower portion 392a forming angle B1 with second foot 394. Second foot 394 has a recess (not shown) for receiving pin 170 and is similar to recess 293 of tool 290 described above. Second arm 392 has an upper portion 392c that terminates with handle 405. Upper portion 392c has ratchet bar 401 with serrations 404. Ratchet bar 401 is pivotally coupled to arm 392 and spring-biased towards projection 403. Ratchet bar 401 is similar to ratchet bar 301, but is preferably curved along its length to accommodate the angular offsets in arms 391, 392 while maintaining engagement between ratchet bar 401 and projection 403. Arm 392 has a vertical extension 392b extending between lower portion 392a and upper portion 392c. Angle B2 is formed between lower portion 392a and vertical portion 392b. Angle B1 is formed between vertical portion 392b and upper portion 392c. Vertical portion 392b as a slot 395 of receiving reduced thickness portion 399 of vertical portion 391b, where first and second arms are pivotally coupled via a pin (not shown.)

In one specific embodiment of compression tool 290 and 390, angle B1 is about 120 degrees and angle B2 is about 150 degrees. However, other angular offsets in first and second arms of compression tools 190, 290 are also contemplated herein as would occur to those skilled in the art.

While the invention has been illustrated and described in detail in the drawings and foregoing description, the same is to be considered as illustrative and not restrictive in character, it being understood that only the preferred embodiment has been shown and described and that all changes and modifications the come within the spirit of the invention are desired to be protected.

What is claimed is:

1. A bone fixation system for a portion of the spinal column, comprising:

a plate having a length along a central axis extending longitudinally between a first end and a second end, and a top surface and a bottom surface along said length, and said plate having a plurality of first openings and a plurality of second openings between said surfaces, therein:

at least one of said plurality of first openings is positioned adjacent said first end, said one first opening defining a circular hole having a first diameter adjacent said bottom surface;

at least one of said plurality of second openings is positioned adjacent said second end, said one second opening defining a slot having a first width and a first length adjacent said bottom surface; and bone engaging fasteners extending through said first and second openings, each bone engaging fastener having an elongated shank defining bone engaging threads thereon and an enlarged head, said shank having a substantially cylindrical portion with a second diameter less than said first diameter so said bone engaging fastener can be inserted through said one first opening and said cylindrical portion contacts said plate in said one first opening so that said bone engaging fastener assumes a fixed orientation relative to said plate, said cylindrical portion second diameter also less than said first width so said bone engaging fastener can be inserted through said one second opening from said top surface of said plate and said head of said bone engaging fastener is translatable along the length of said at least one second opening to maintain compression of the spinal column portion, wherein said second openings include a ramp that guides said bone engaging fastener as it is inserted into said one second opening to provide a dynamic compression load to the spinal column portion.

2. The bone fixation system of claim 1, whereby each of said at least one first and second openings define a recess adjacent said top surface and said enlarged head defines a partially spherical surface complementary to said recess of said at least one first and second openings.

3. The bone fixation system of claim 2, wherein said head of said fastener includes a truncated top surface.

4. The bone fixation system of claim 2, further comprising a retainer assembly for retaining said heads of said number of bone engaging fasteners within said at least one first opening and said at least one second opening.

5. The bone fixation system of claim 4, wherein said retainer assembly includes:

a first fastener bore defined in said plate adjacent said at least one first opening and a second fastener bore defined in said plate adjacent said at least one second opening;

a washer having at least a first aperture adjacent said at least one first opening and a second aperture adjacent said at least one second opening and a countersink portion communicating with each of said apertures, said washer further having a body with portions overlapping said at least one first and second opening when said washer is in a first position relative to said at least one first and second openings, said body portions being arranged so that bone engaging fasteners can be inserted through said at least one first opening and said at least one second opening when said washer is in a second position relative to said at least one first and second openings; and a locking fastener for each of said apertures having a head configured to be at least partially recessed within said countersink portion of said washer and having an elongated shank extending through said aperture and configured to engage said fastener bore of said plate.

6. The bone fixation system of claim 5, wherein said plate further defines a groove in said top surface extending longitudinally along said plate, said groove being overlapping said at least one first and second openings, said first and second fastener bores being positioned within said groove.

7. The bone fixation system of claim 4, wherein said retainer assembly includes a washer having a contact surface for contacting said head of said bone engaging fastener in said one first opening and an outer surface for overlapping said heads of said bone engaging fasteners in said one second opening.

8. The bone fixation system of claim 1, further comprising a retainer assembly including:

a first fastener bore defined in said plate adjacent said at least one first opening and a second fastener bore defined in said plate adjacent said at least one second opening;

a washer having at least a first aperture adjacent said at least one first opening and a second aperture adjacent said at least one second opening and a countersink communicating with each of said apertures, said washer further having a surface configured to contact said head of said bone engaging fastener extending through said at least one first opening; and a locking fastener for each of said apertures having a head configured to be at least partially recessed within said countersink portion of said washer and an elongated shank extending through said aperture configured to engage said fastener bore of said plate.

9. The bone fixation system of claim 8, wherein said washer has an outer surface that overlaps said head of said bone engaging fastener extending through said at least one second hole without contacting said head.

10. The bone fixation system of claim 8, wherein said plate further defines a groove in said top surface extending longitudinally along said plate, said groove overlapping said at least one first and second openings, said first and second fastener bores being positioned within said groove.

11. The bone fixation system of claim 1, wherein said elongated plate defines a plurality of vertebral nodes at longitudinally spaced locations along the plate.

12. The bone fixation system of claim 11, wherein there are provided a pair of said first openings at one of said vertebral nodes adjacent said first end of said plate and a pair of said second openings at one of said vertebral nodes adjacent said second end of said plate.

13. The bone fixation system of claim 12, wherein said openings of said pair of first openings are symmetrically positioned about said central axis and said openings of said pair of second openings are symmetrically positioned about said central axis.

14. The bone fixation system of claim 1, further comprising an implant positionable within the spinal column.

15. The bone fixation system of claim 14, wherein the implant comprises an implant selected from the group consisting of a bone graft, a fusion device, and an interbody device.

16. A bone fixation system for a portion of the spinal column, comprising:
a plate having a length along a central axis extending longitudinally between a first end and a second end, a top surface and a bottom surface along said length, said plate further defining a plurality of first openings and a plurality of second openings between said surfaces, wherein:
at least two of said first openings are circular, having a first diameter, and are positioned adjacent said first end;
at least two of said second openings are slotted, having a first width and a first length, and are positioned adjacent said second end of said plate;
bone engaging fasteners extending through said first and second openings, each bone engaging fastener having an elongated shank having bone engaging threads thereon and an enlarged head, said bone engaging fasteners configured for insertion into said first and second openings from said top surface; and
means retaining said heads of said bone engaging fasteners in said first and second openings, said retaining means translatable from a first position allowing bone engaging fastener insertion into said first and second openings to a second position retaining said bone engaging fasteners in said first and second openings.

17. The bone fixation system of claim 16, wherein said two first openings have a recess portion adjacent said top surface and said two second openings have a recess portion adjacent said top surface.

18. The bone fixation system of claim 17, wherein said heads of said bone engaging fasteners are configured to be at least partially recessed in said two first and second openings.

19. The bone fixation system of claim 16, wherein said two first and second openings each include a recess adjacent said top surface and said enlarged head has a partially spherical surface complementary to said recess of said two first and second openings.

20. The bone fixation system of claim 19, wherein said plate further defines a groove in said top surface extending longitudinally along said plate for receiving said retaining means therein, said retaining means overlapping said recesses.

21. The bone fixation system of claim 16, wherein said head of said bone engaging fastener has an inclined surface and said retaining means has a contact surface to contact said inclined surface of said bone engaging fasteners extending through said two first openings.

22. The bone fixation system of claim 16, wherein said retaining means includes:
a first fastener bore defined in said plate adjacent said two first openings and a second fastener bore defined in said plate adjacent said two second openings;
a washer having a body defining at least a first aperture adjacent said two first openings and a second aperture adjacent said two second openings and a countersink portion communicating with each of said apertures, said washer further having a contact surface configured to contact said head of said bone engaging fastener extending through said two first openings; and
a locking fastener for each of said apertures having a head configured to be at least partially recessed within said countersink portion of said washer and an elongated shank extending through said aperture and configured to engage said fastener bore of said plate.

23. The bone fixation system of claim 22, wherein said apertures of said washer each form a slot having a length extending longitudinally with the plate.

24. The bone fixation system of claim 23, wherein at least one of said aperture countersink portions is tapered along said length of said slot and has a width that increases along said length of said aperture from said second end towards said first end.

25. The bone fixation system of claim 23, wherein said at least one aperture is positioned adjacent said two second openings.

26. The bone fixation system of claim 16, wherein said retaining means includes:
a first fastener bore defined in said plate adjacent said two first openings and a second fastener bore defined in said plate adjacent said two second openings;
a washer having at least a first aperture adjacent said two first openings and a second aperture adjacent said two second openings and a countersink portion communicating with each of said apertures, said washer further having a body with portions overlapping said two first openings and said two second openings when said washer is in a first position relative to said two first and second openings, said body portions being arranged so that bone engaging fasteners can be extended through said two first openings and said two second openings when said washer is in a second position relative to said two first and second openings; and
a locking fastener for each of said apertures having a head configured to be at least partially recessed within said tapered portion of said washer and an elongated shank extending through said aperture and configured to engage said fastener bore of said plate.

27. The bone fixation system of claim 26, wherein said apertures of said washer form slots having a length extending in the direction of the length of the plate.

28. The bone fixation system of claim 27, where said countersink communicating with each of said apertures has a width that increases along the length of said-aperture in a direction from said second end towards said first end.

29. The bone fixation system of claim 16, further comprising an implant positionable within the spinal column.

30. The bone fixation system of claim 29, wherein the implant comprises an implant selected from the group consisting of a bone graft, a fusion device, and an interbody device.

31. A bone fixation system for a portion of the spinal column, comprising:
four bone engaging fasteners, each having an enlarged head and a threaded shank;
an elongated plate having a length extending between a first end and a second end and sized to span between at least two vertebrae, said plate defining a one pair of adjacent holes adjacent said first end and one pair of adjacent slots adjacent said second end, each of said holes and said slots configured to receive said threaded shank of a corresponding one of said bone engaging fasteners therethrough, wherein said bone engaging fasteners extending through said pair of holes fix said plate to said first vertebra and said bone engaging fasteners extend through said slots to secure said plate to said second vertebra, and said bone engaging fasteners received in said slots are enabled to translate in said slots in a direction of the length of the plate to maintain compression on the spinal column portion; and a retainer assembly having a retainer mechanism configured to overlap each of said holes and slots and retain said bone engaging fasteners extending through said holes and slots.

32. The bone fixation system of claim 31, wherein said plate has a top surface and a bottom surface and said holes and said slots each further include a recess adjacent said top surface.

33. The bone fixation system of claim 31, wherein said head of each of said bone engaging fasteners has an inclined surface and said retainer mechanism has a contact surface configured to contact said inclined surface of said bone engaging fasteners extending through said pair of holes.

34. The bone fixation system of claim 31, wherein said plate includes a first fastener bore defined in said plate between said pair of holes and a second fastener bore defined in said plate between said pair of slots, and said retainer assembly further includes:

said retainer mechanism has at least a first aperture adjacent said holes and a second aperture adjacent said slots and a countersink portion communicating with each of said apertures; and a locking fastener for each of said apertures, said locking fastener having a head configured to be recessed within said recess of said retainer mechanism and an elongated shank extending through said aperture and configured to engage said fastener bore of said plate.

35. The bone fixation system of claim 34, wherein said elongated shank of said locking fastener terminates in a sharp point for penetrating a vertebral body.

36. The bone fixation system of claim 35, wherein said head of said locking fastener defines a lower conical surface for contacting said retainer mechanism.

37. The bone fixation system of claim 31, further comprising an implant positionable within the spinal column.

38. The bone fixation system of claim 37, wherein the implant comprises an implant selected from the group consisting of a bone graft, a fusion device, and an interbody device.

39. A bone fixation system for a portion of a spinal column, comprising:

six bone engaging fasteners, each having an enlarged head and a threaded shank;

an elongated plate having a length extending between a first end and a second end and sized to span between at least three vertebrae, said plate defining one pair of holes over a first vertebra, one pair of into slots over a second vertebra, and one pair of slots over a third vertebra, each of said holes and said slots configured to receive said threaded shank of a corresponding one of said bone engaging fasteners therethrough, wherein said bone engaging fasteners extending through said pair of holes fix said plate to said first vertebra and said bone engaging fasteners extend through said slots to secure said plate to said second vertebra, and said bone engaging fasteners received in said slots are enabled to translate in said slots in a direction of the length of the plate to maintain compression on the spinal column portion; and a retainer assembly having a retainer mechanism configured to overlap each of said holes and slots and retain said bone engaging fastener extending through said holes and slots in said plate.

40. The bone fixation system of claim 39, further comprising an implant positionable within the spinal column.

41. The bone fixation system of claim 40, wherein the implant comprises an implant selected from the group consisting of a bone graft, a fusion device, and an interbody device.

42. A fastener retainer assembly for an elongated plate having a length extending between at least two vertebrae, the plate defining a number of openings therethrough for insertion of bone engaging fasteners to attach the plate to the at least two vertebrae, said retainer assembly comprising:

a first fastener bore defined in said plate adjacent at least one of the openings positioned over the first vertebra and a second fastener bore defined in said plate adjacent at least one the openings positioned over the second vertebra;

a washer defining at least a first aperture adjacent said at least one opening positioned over the first vertebra and a second aperture adjacent said at least one opening positioned over the second vertebra, said washer configured to retain said bone engaging fasteners extending through said openings in said plate; and a locking fastener for each of said apertures, said locking fastener having an elongated shank extending through said aperture and configured to engage said fastener bore of said plate, said openings in said plate being positioned and configured wherein said washer is movable between a first position enabling insertion of said bone engaging fasteners into said at least one openings and a second position wherein said washer retains said inserted bone engaging fasteners in said plate.

43. The retainer assembly of claim 42, wherein said apertures of said washer form slots having a length extending in the direction of the length of the plate.

44. The retainer assembly of claim 43, wherein each of said apertures include a countersink portion communication with said slot.

45. The retainer assembly of claim 44, wherein said countersink portion of at least one of said apertures is tapered and has a width that increases along the length of said aperture from a second end to a first end.

46. A fastener retainer assembly for an elongated plate extending between at least two vertebrae, the plate defining a number of openings for insertion of bone engaging fasteners therethrough to secure the plate to the at least two vertebrae, and the plate defining at least one fastener bore, said retainer assembly comprising:

a washer having a central axis and defining at least a first aperture in communication with said at least one fastener bore, said washer further configured to retain said heads of at least two bone engaging fasteners extending through certain ones of said openings in said plate; and a locking fastener for said first aperture having an elongated shank extending through said aperture and configured to engage said fastener bore of said plate, said washer being movable along said central axis between a first position whereby said at least two bone engaging fasteners are insertable into certain ones of said openings and a second position whereby washer retains said at least two bone engaging fasteners in said plate.

47. The retainer assembly of claim 46, wherein said apertures of said washer form slots having a length extending in the direction of the length of the plate.

48. The retainer assembly of claim 47, wherein each of said apertures include a countersink portion communication with said slot.

49. The retainer assembly of claim 47, wherein said countersink portion of at least one of said apertures is tapered and has a width that increases along the length of said aperture from a second end to a first end.

50. A plating system for the spinal column, comprising:
   a plate having a length along a central axis extending longitudinally between a first end and a second end, the plate having a top surface and a bottom surface along the length;
   a first fixation system for fastening the plate and a first portion of the spinal column in a fixed position;
   a second fixation system for fastening the plate and a second portion of the spinal column in a translatable position; and
   a retainer mechanism movably fixed to the plate, the retainer mechanism movable between a first position and a second position, wherein the retainer mechanism in the second position maintains at least a portion of at least one of the first fixation system and the second fixation system in a predetermined relative position with respect to the plate.

51. The plating system of claim 50, wherein the first fixation system comprises a first bone engaging fastener fixedly engaging the plate and wherein the second fixation system comprises a second bone engaging fastener translatably engaging the plate.

52. The plating system of claim 50, wherein the second fixation system comprises an opening having an opening width and an opening length, the opening length extending substantially longitudinally, and wherein the opening length is greater than the opening width.

53. The plating system of claim 50, wherein the first fixation system comprises a first opening in the plate defining a first opening size, and wherein the second fixation system comprises a second opening in the plate defining a longitudinally-extending slot having a slot length.

54. The plating system of claim 53, wherein the first fixation system further comprises a first fastening mechanism for connecting the plate and the spinal column, the first fastening mechanism comprising a first body extendable through the first opening in the plate, the first body having a first body size substantially equal to the first opening side, and wherein the second fixation system further comprises a second fastening mechanism connecting the plate and the spinal column, the second fastening mechanism comprising a second body extendable through the second opening in the plate, the second body having a second body size substantially less than the slot length.

55. The plating system of claim 50, further comprising an implant positionable within the spinal column.

56. The plating system of claim 55, wherein the implant comprises an implant selected from the group consisting of a bone graft, a fusion device, and an interbody device.

57. The plating system of claim 50, wherein the retainer mechanism further comprises:
   a translatable body, wherein in the second position the translatable body interferes with the portion of at least one of the first fixation system and the second fixation system; and
   a movable locking mechanism, wherein in the second position the movable locking mechanism holds the translatable body at a fixed position.

58. The plating system of claim 50, wherein the predetermined relative position for the portion of at least one of the first fixation system and the second fixation system comprises a position between the plate and the retainer mechanism.

59. The plating system of claim 56, further comprising:
   a third fixation system for fastening the plate and a third portion of the spinal column in a translatable position, wherein the third fixation system is independently translatable with respect to the second fixation system.

60. The plating system of claim 59, wherein the first fixation system comprises a first bone engaging fastener and a circular hole within the plate, the first bone engaging fastener having a first head engageable with the circular hole, and wherein at least one of the second fixation system and the third fixation system comprises a second bone engaging fastener and a slot within the plate, the second bone engaging fastener having a second head translatably engageable with the slot.

61. The plating system of claim 59, wherein the first fixation system, the second fixation system and the third fixation system each include at least one bone engaging fastener and corresponding holes within the plate, and wherein the retainer mechanism is translatable along the length of the plate between a first position and a second position, wherein in the first position the retainer mechanism allows movement- of the bone engaging fasteners into and out of the holes in the plate, and wherein in the second position the retainer mechanism secures the bone engaging fasteners within the holes in the plate.

62. The plating system of claim 59, wherein the first fixation system is longitudinally spaced from the second fixation system and the third fixation system such that the first fixation system defines a position of a first vertebral node and the second fixation system and the third fixation system respectively define positions of adjacent portions of a second vertebral node.

63. A plating system for the spinal column, comprising:
   a plate having a length along a central axis extending longitudinally between a first end and a second end, the plate having a top surface and a bottom surface along the length;
   a first fixation system for fastening the plate and a first portion of the spinal column in a fixed position,
   a second fixation system for fastening the plate and a second portion of the spinal column in a translatable position; and
   a retainer mechanism movably fixed to the plate, the retainer mechanism translatable between a first position and a second position, wherein the retainer mechanism in the second position confines at least a portion of both the first fixation system and the second fixation system within a predetermined range of positions relative to the top surface of the plate.

64. The plating system of claim 63, wherein the predetermined range of positions comprise positions between the plate and the retainer mechanism.

65. The plating system of claim 64, wherein the first fixation system comprises a first bone engaging fastener and a first opening within the plate, the first bone engaging fastener and the first opening both sized such that the first bone engaging fastener maintains a substantially fixed orientation within the first opening, and- wherein the second fixation system comprises a second bone engaging fastener and a second opening both sized such that the second bone engaging fastener is translatable along at least a portion of the length of the plate within the second opening.

66. The plating system of claim 65, wherein the second opening further comprises a ramp for engaging the second bone engaging fastener and for applying a dynamic compression load to the spinal column upon insertion of the second bone engaging screw.

67. The plating system of claim 65, wherein the second fixation system further comprises a third bone engaging fastener and a third opening both sized such that the third bone engaging fastener is translatable along at least a portion of the length of the plate within the third opening.

68. The plating system of claim 67, wherein the second bone engaging fastener is independently translatable with respect to the third bone engaging fastener.

69. The plating system of claim 68, wherein the first opening is longitudinally spaced from the second opening and the third opening such that the first opening defines a first vertebral node and the second opening and the third opening define adjacent portions of a second vertebral node.

70. The plating system of claim 65, wherein the translation of the retainer mechanism between the first position and the second position is in a direction along the length of the plate.

71. The plating system of claim 70, further comprising an implant positionable within the spinal column.

72. The plating system of claim 65, further comprising an implant positionable within the spinal column.

73. A plating system for the spinal column, comprising:
  a plate having a length along a central axis extending longitudinally between a first end and a second end, the plate having a top surface and a bottom surface along the length;
  a first fixation system fastenable in a fixed position with respect to the plate and mountable to a first portion of the spinal column;
  a second fixation system fastenable in a translatable position with respect to the plate and mountable to a second portion of the spinal column;
  a retainer body movable between a first position and a second position, wherein in the second position the retainer body maintains at least a portion of at least one of the first fixation system and the second fixation system in a predetermined position relative to the plate.

74. The plating system of claim 73, further comprising a locking mechanism fixable to the plate and movable between a third position and a fourth position, wherein in the third position the retainer body is movable between the first position and the second position, and wherein in the fourth position the locking mechanism holds the retainer body in a fixed position.

75. The plating system of claim 73, further comprising an implant positionable within the spinal column.

76. The plating system of claim 75, wherein the implant comprises an implant selected from the group consisting of a bone graft, a fusion device, and an interbody device.

77. The plating system of claim 73, wherein the predetermined position of at least the portion of at least one of the first fixation system and the second fixation system comprises a position located between the plate and the retainer body.

78. The plating system of claim 77, wherein the first fixation system comprises a first bone engaging fastener and a first opening within the plate, and wherein the second fixation system comprises a second bone engaging fastener and a second opening within the plate, wherein the second opening comprises an elongated hole extending along at least a portion of the length of the plate, and wherein the second bone engaging fastener is translatably engagable with the second opening.

79. The plating system of claim 78, wherein the first bone engaging fastener further comprises a first head sized greater than the first opening, and wherein the second bone engaging fastener comprises a second head sized for translatable engagement with the second opening, and wherein the second head comprises the portion of the second fixation system maintained in the predetermined position by the retainer body.

80. The plating system of claim 78, wherein the second opening further comprises a ramp for engaging the second bone engaging fastener and for applying a dynamic compression load to the spinal column upon insertion of the second bone engaging screw.

81. The plating system of claim 78, wherein the second fixation system further comprises a third bone engaging fastener and a third opening both sized such that the third bone engaging fastener is translatable along at least a portion of the length of the plate within the third opening.

82. The plating system of claim 81, wherein the second bone engaging fastener is independently translatable with respect to the third bone engaging fastener.

83. The plating system of claim 82, wherein the first opening is longitudinally spaced from the second opening and the third opening such that the first opening defines a first vertebral node and the second opening and the third opening define adjacent portions of a second vertebral node.

84. The plating system of claim 78, wherein the translation of the retainer body between the first position and the second position is in a direction along the length of the plate.

85. The plating system of claim 78, wherein the retainer body is fixable to the plate.

86. A bone fixation system for a portion of the spinal column, comprising:
  a plate having a length along a central axis extending longitudinally between a first end and a second end, and a top surface and a bottom surface along said length, and said plate having a plurality of first openings and a plurality of second openings between said surfaces, wherein:
  at least one of said plurality of first openings is positioned adjacent said first end, said one first opening defining a circular hole having a first diameter adjacent said bottom surface;
  at least one of said plurality of second openings is positioned adjacent said second ends said one second opening defining a slot having a first width and a first length adjacent said bottom surface;
  bone engaging fasteners extending through said first and second openings, each bone engaging fastener having an elongated shank defining bone engaging threads thereon and an enlarged head, said shank having a substantially cylindrical portion with a second diameter less than said first diameter so said bone engaging fastener can be inserted through said one first opening and said cylindrical portion contacts said plate in said one first opening so that said bone engaging fastener assumes a fixed orientation relative to said plate, said cylindrical portion second diameter also less than said first width so said bone engaging fastener can be inserted through said one second opening from said top surface of said plate and said head of said bone engaging fastener is translatable along the length of said at least one second opening to maintain compression of the spinal column portion;

whereby each of said at least one first and second opening defines a recess adjacent said top surface and said enlarged head defines a partially spherical surface complementary to said recess of said at least one first and second openings; and a retainer assembly for retaining said heads of said number of bone engaging fasteners within said at least one first opening and said at least one second opening.

87. The bone fixation system of claim 86, wherein said retainer assembly includes:

a first fastener bore defined in said plate adjacent said at least one first opening and a second fastener bore defined in said plate adjacent said at least one second opening;

a washer having at least a first aperture adjacent said at least one first opening and a second aperture adjacent said at least one second opening and a countersink portion communicating with each of said apertures, said washer further having a body with portions overlapping said at least one first and second opening when said washer is in a first position relative to said at least one first and second openings, said body portions being arranged so that bone engaging fasteners can be inserted through said at least one first opening and said at least one second opening when said washer is in a second position relative to said at least one first and second openings; and a locking fastener for each of said apertures having a head configured to be at least partially recessed within said countersink portion of said washer and having an elongated shank extending through said aperture and configured to engage said fastener bore of said plate.

88. The bone fixation system of claim 87, wherein said plate further defines a groove in said top surface extending longitudinally along said plate, said groove overlapping said at least one first and second openings, said first and second fastener bores being positioned within said groove.

89. The bone fixation system of claim 86, wherein said retainer assembly includes a washer having a contact surface for contacting said head of said bone engaging fastener in said one first opening and an outer surface for overlapping said heads of said bone engaging fasteners in said one second opening.

90. A bone fixation system for a portion of the spinal column, comprising:

a plate having a length along a central axis extending longitudinally between a first end and a second end, and a top surface and a bottom surface along said length, and said plate having a plurality of first openings; and a plurality of second open between said surfaces, wherein:

at least one of said plurality of first openings is positioned adjacent said first end, said one first opening defining a circular hole having a first diameter adjacent said bottom surface;.

at least one of said plurality of second openings is positioned adjacent said second end, said one second opening defining a slot having a first width and a first length adjacent said bottom surface;

bone engaging fasteners extending through said first and second openings, each bone engaging fastener having an elongated shank defining bone engaging threads thereon and an enlarged head, said shank having a substantially cylindrical portion with a second diameter less than said first diameter so said bone engaging fastener can be inserted through said one first opening and said cylindrical portion contacts said plate in said one first opening so that said bone engaging fastener assumes a fixed orientation relative to said plate, said cylindrical portion second diameter also less than said first width so said bone engaging fastener can be inserted through said one second opening from said top surface of said plate and said head of said bone engaging fastener is translatable along the length of said at least one second opening to maintain compression of the spinal column portion; and a retainer assembly including:

a first fastener bore defined in said plate adjacent said at least one first opening and a second fastener bore defined in said plate adjacent said at least one second opening;

a washer having at least a first aperture adjacent said at least one first opening and a second aperture adjacent said at least one second opening and a countersink communicating with each of said apertures, said washer further having a surface configured to contact said head of said bone engaging fastener extending through said at least one first opening; and a locking fastener for each of said apertures having a head configured to be at least partially recessed within said countersink portion of said washer and an elongated shank extending through said aperture configured to engage said fastener bore of said plate.

91. The bone fixation system of claim 90, wherein said washer has an outer surface that overlaps said head of said bone engaging fastener extending through said at least one second hole without contacting said head.

92. The bone fixation system of claim 90, wherein said plate further defines a groove in said top surface extending longitudinally along said plate, said groove overlapping said at least one first and second openings, said first and second fastener bores being positioned within said groove.

* * * * *